(12) United States Patent
Mura et al.

(10) Patent No.: US 11,311,243 B2
(45) Date of Patent: Apr. 26, 2022

(54) BLOOD PRESSURE DATA PROCESSING APPARATUS, BLOOD PRESSURE DATA PROCESSING METHOD, AND BLOOD PRESSURE DATA PROCESSING PROGRAM

(71) Applicant: OMRON HEALTHCARE CO., LTD., Muko (JP)

(72) Inventors: Seitaro Mura, Kyoto (JP); Hirotaka Wada, Kyoto (JP); Eriko Kan, Kyoto (JP); Ayako Kokubo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 335 days.

(21) Appl. No.: 16/561,460

(22) Filed: Sep. 5, 2019

(65) Prior Publication Data

US 2020/0008748 A1 Jan. 9, 2020

Related U.S. Application Data

(63) Continuation of application No. PCT/JP2018/009584, filed on Mar. 12, 2018.

(30) Foreign Application Priority Data

Mar. 14, 2017 (JP) .............................. JP2017-049012

(51) Int. Cl.
*A61B 5/00* (2006.01)
*A61B 5/0205* (2006.01)
(Continued)

(52) U.S. Cl.
CPC ............ *A61B 5/721* (2013.01); *A61B 5/0205* (2013.01); *A61B 5/113* (2013.01); *A61B 5/725* (2013.01);
(Continued)

(58) Field of Classification Search
CPC ....... A61B 5/721; A61B 5/0205; A61B 5/113; A61B 5/725; A61B 5/7257; A61B 5/1118;
(Continued)

(56) References Cited

U.S. PATENT DOCUMENTS

| 6,081,742 A * | 6/2000 | Amano ................ A61B 5/0205 600/484 |
| 2016/0213332 A1* | 7/2016 | Ukawa ................. A61B 5/0205 |
| 2017/0273582 A1* | 9/2017 | Kawamoto ........ A61B 5/02108 |

FOREIGN PATENT DOCUMENTS

| JP | 2002-224059 A | 8/2002 |
| JP | 2007-330432 A | 12/2007 |

(Continued)

OTHER PUBLICATIONS

Jun. 5, 2018 International Search Report issued in International Patent Application No. PCT/JP2018/009584.

*Primary Examiner* — Sean P Dougherty
*Assistant Examiner* — Kyle W. Kretzer
(74) *Attorney, Agent, or Firm* — Oliff PLC

(57) ABSTRACT

A blood pressure data processing apparatus including a peak selection unit, a frequency component suppression unit, a respiratory fluctuation calculation unit, an attenuation amount calculation unit, and a respiratory cycle determination unit. The frequency component suppression unit suppresses components of the selected peak frequency within the first spectrum, and generates a second spectrum. The respiratory fluctuation calculation unit calculates a first respiratory fluctuation in second blood pressure data, and calculates a second respiratory fluctuation in third blood pressure data, which is a time domain representation of the second spectrum. The attenuation amount calculation unit calculates an attenuation amount of the second respiratory fluctuation relative to the first respiratory fluctuation. The respiratory cycle determination unit determines a cycle (Continued)

corresponding to the selected peak frequency as a respiratory cycle of a user if the attenuation amount is greater than a threshold.

9 Claims, 23 Drawing Sheets

(51) Int. Cl.
    *A61B 5/113*     (2006.01)
    *A61B 5/021*     (2006.01)
    *A61B 5/08*     (2006.01)
    *A61B 5/11*     (2006.01)

(52) U.S. Cl.
    CPC ............ *A61B 5/7257* (2013.01); *A61B 5/021* (2013.01); *A61B 5/02108* (2013.01); *A61B 5/0816* (2013.01); *A61B 5/1118* (2013.01); *A61B 5/7203* (2013.01); *A61B 2562/0219* (2013.01); *A61M 2230/00* (2013.01)

(58) Field of Classification Search
    CPC ..... A61B 5/7203; A61B 5/021; A61B 5/0816; A61B 2562/0219; A61B 5/02108; A61B 5/022; A61M 2230/00
    See application file for complete search history.

(56) References Cited

FOREIGN PATENT DOCUMENTS

| | | |
|---|---|---|
| JP | 2016-137087 A | 8/2016 |
| WO | 98/10699 A1 | 3/1998 |

\* cited by examiner

FIG. 5A
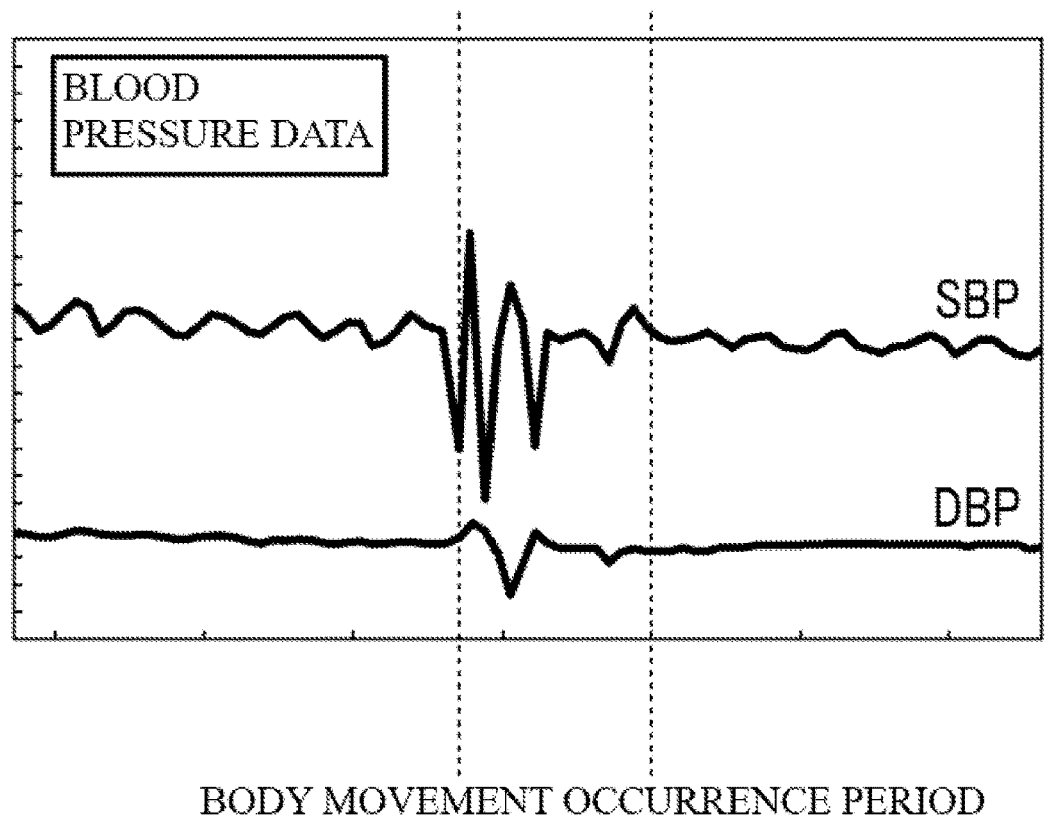
BODY MOVEMENT OCCURRENCE PERIOD
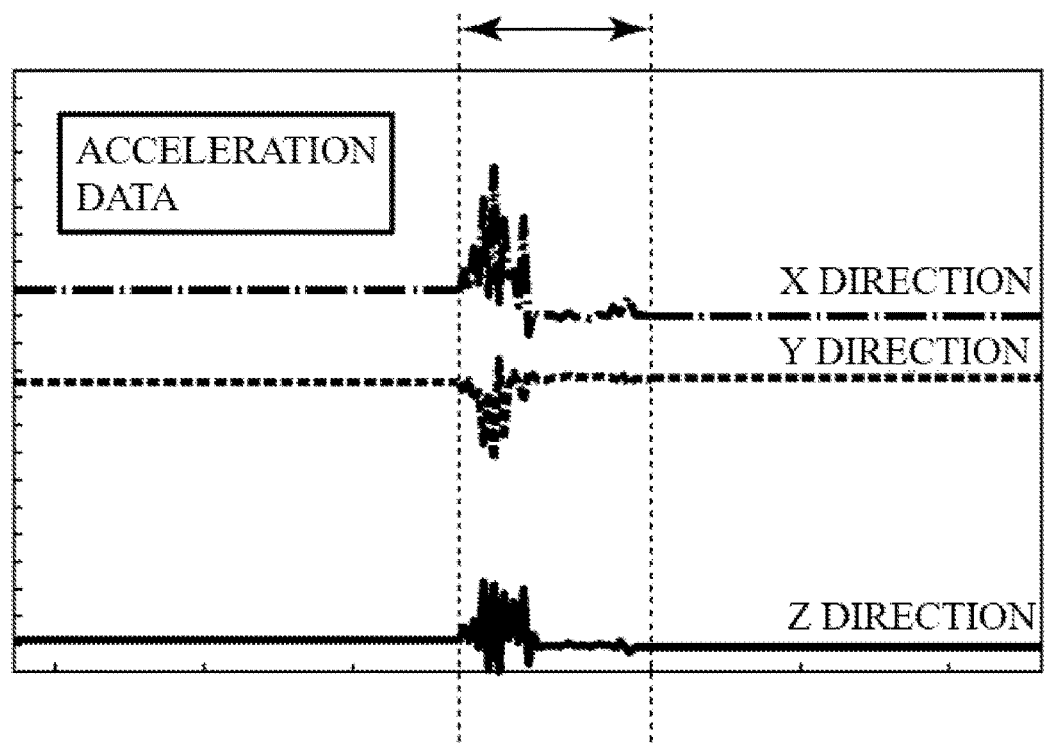
FIG. 5B

BLOOD PRESSURE DATA PROCESSING APPARATUS, BLOOD PRESSURE DATA PROCESSING METHOD, AND BLOOD PRESSURE DATA PROCESSING PROGRAM

TECHNICAL FIELD

The present invention relates to processing blood pressure data.

BACKGROUND ART

Patients with blood pressure disorders (typically, high blood pressure) desirably manage their blood pressure on a daily basis. Conventional stationary blood pressure measuring apparatuses are not suitable for users to carry around with them, and thus measuring blood pressure away from home such as at work or on an outing is a significant encumbrance for users. Also, sudden fluctuations in blood pressure that can increase the onset risk of cerebrovascular and cardiovascular disease are extremely difficult to pick up on simply by measuring blood pressure several times a day.

In recent years, user terminals capable of measuring the blood pressure of a user simply by being worn on the user's wrist, for example, have been realized, following advances in sensor technology. Such user terminals enable blood pressure to be measured on a timely basis, without significantly encumbering users. There are also user terminals that are able to continuously measure blood pressure per beat, using techniques such as the tonometry method, for example.

Blood pressure is known to fluctuate with breathing. Specifically, systolic blood pressure at the time of inhalation drops by about 3 to 9 mmHg compared with systolic blood pressure at the time of exhalation (respiratory fluctuation). Respiratory fluctuation may possibly become an impediment to the analysis of blood pressure data for detecting the occurrence of the aforementioned sudden fluctuations in blood pressure. It may be sought to suppress respiratory fluctuation included in blood pressure data for this reason.

On the other hand, the phenomena where respiratory fluctuation exceeds 10 mmHg is called pulsus *paradoxus* (PP). Pulsus *paradoxus* is used in diagnosing disorders such as asthma, chronic obstructive pulmonary disease (COPD), and cardiac tamponade. It may also be sought to extract respiratory fluctuation from blood pressure data for this reason.

SUMMARY OF INVENTION

Technical Problem

If there is body movement in the user, the accuracy of blood pressure measurement may drop due to noise such as oscillation of blood vessels occurring. In particular, in the case of continuously measuring the blood pressure of a user, the user may not always be in a resting state, and thus the blood pressure data may possibly include both reliable data and unreliable data. Also, the breathing cycle not only differs between individuals, but can also change depending on the mental and physical state or the environment of the same user. Thus, in the case of analyzing this blood pressure data, difficulties could be encountered in correctly inferring and suppressing/extracting respiratory fluctuation.

An object of the present invention is to infer the respiratory cycle of a user.

Solution to Problem

According to a first aspect of the present invention, a blood pressure data processing apparatus includes a respiratory cycle inference unit configured to infer a respiratory cycle of a user based on a first spectrum, which is a frequency domain representation of second blood pressure data in which noise relating to body movement of the user included in first blood pressure data of the user is suppressed. The respiratory cycle inference unit includes a peak selection unit, a first frequency component suppression unit, a respiratory fluctuation calculation unit, an attenuation amount calculation unit, and a respiratory cycle determination unit. The peak selection unit is configured to select one of peak frequencies indicating a peak in power spectra of the first spectrum. The first frequency component suppression unit is configured to suppress a component of the selected peak frequency within the first spectrum, and generate a second spectrum. The respiratory fluctuation calculation unit is configured to calculate a first respiratory fluctuation in the second blood pressure data, and calculate a second respiratory fluctuation in third blood pressure data, which is a time domain representation of the second spectrum. The attenuation amount calculation unit is configured to calculate an attenuation amount of the second respiratory fluctuation relative to the first respiratory fluctuation. The respiratory cycle determination unit is configured to determine a cycle corresponding to the selected peak frequency as the respiratory cycle of the user if the attenuation amount is greater than a first threshold. Therefore, the respiratory cycle can be stably and accurately inferred regardless of factors such as the personal traits or the mental or physical state of the user, or the environment in which blood pressure is measured.

According to a second aspect of the present invention, the respiratory cycle determination unit causes the peak selection unit to select one of unselected peak frequencies if the attenuation amount is less than or equal to the first threshold. Therefore, the respiratory cycle can be inferred more stably and accurately.

According to a third aspect of the present invention, the peak selection unit selects peak frequencies in descending order of frequency. Therefore, the peak frequency corresponding to the respiratory cycle can be searched for efficiently, and an erroneous respiratory cycle being inferred due to blood pressure fluctuation components of the user can be prevented.

According to a fourth aspect of the present invention, the first frequency component suppression unit performs low pass filtering on the first spectrum to generate the second spectrum, and a cutoff frequency of the low pass filtering is set to lower than the selected peak frequency. Therefore, high frequency components including the peak frequency component within the first spectrum can be collectively suppressed.

According to a fifth aspect of the present invention, the blood pressure data processing apparatus further includes a respiratory fluctuation suppression unit configured to generate processed blood pressure data in which respiratory fluctuation of the user included in the second blood pressure data is suppressed. The respiratory fluctuation suppression unit includes a second frequency component suppression unit and a first transformation unit. The second frequency component suppression unit is configured to suppress frequency components that correspond to the respiratory cycle of the user within the first spectrum, and generate a third spectrum. The first transformation unit is configured to transform the third spectrum into a time domain representation, and generate the processed blood pressure data. Therefore, processed blood pressure data in which the respiratory fluctuation of the user is suppressed can be obtained.

According to a sixth aspect of the present invention, the blood pressure data processing apparatus further includes a respiratory fluctuation extraction unit configured to extract respiratory fluctuation of the user included in the second blood pressure data, and generate respiratory fluctuation data. The respiratory fluctuation extraction unit includes a third frequency component suppression unit and a second transformation unit. The third frequency component suppression unit is configured to suppress frequency components that do not correspond to the respiratory cycle of the user within the first spectrum, and generate a fourth spectrum. The second transformation unit is configured to transform the fourth spectrum into a time domain representation, and generate the respiratory fluctuation data. Therefore, respiratory fluctuation data from which the respiratory fluctuation of the user has been extracted can be obtained.

According to a seventh aspect of the present invention, the blood pressure data processing apparatus further includes a setting unit, a respiratory fluctuation suppression unit, and a respiratory fluctuation extraction unit. The setting unit is configured to set a first control parameter indicating that processing for suppressing the respiratory fluctuation of the user included in the second blood pressure data is enabled/disabled, and a second control parameter indicating that processing for extracting the respiratory fluctuation is enabled/disabled. The respiratory fluctuation suppression unit is configured to, in a case where the first control parameter indicates enabled, generate processed blood pressure data in which the respiratory fluctuation of the user included in the second blood pressure data is suppressed. The respiratory fluctuation extraction unit is configured to, in a case where the second control parameter indicates enabled, extract the respiratory fluctuation and generate respiratory fluctuation data. The respiratory fluctuation suppression unit includes a second frequency component suppression unit and a first transformation unit. The second frequency component suppression unit is configured to suppress frequency components that correspond to the respiratory cycle of the user within the first spectrum, and generate a third spectrum. The first transformation unit is configured to transform the third spectrum into a time domain representation, and generate the processed blood pressure data. The respiratory fluctuation extraction unit includes a third frequency component suppression unit and a second transformation unit. The third frequency component suppression unit is configured to suppress frequency components that do not correspond to the respiratory cycle of the user within the first spectrum, and generate a fourth spectrum. The second transformation unit is configured to transform the fourth spectrum into a time domain representation, and generate the respiratory fluctuation data. Therefore, processed blood pressure data and respiratory fluctuation data can both be obtained as needed.

According to an eighth aspect of the present invention, the blood pressure data processing apparatus further includes a body movement noise suppression unit configured to suppress noise relating to body movement of the user included in the first blood pressure data, and generate the second blood pressure data. The body movement noise suppression unit includes a body movement determination unit and a blood pressure data interpolation unit. The body movement determination unit is configured to determine whether body movement of the user has occurred in a unit period, based on body movement data obtained from a motion sensor worn by the user. The blood pressure data interpolation unit is configured to generate blood pressure data through interpolation for a unit period with respect to which it is determined that body movement of the user has occurred, and replace the first blood pressure data of the unit period with the blood pressure data generated through interpolation to generate the second blood pressure data. Therefore, blood pressure data of the body movement occurrence period can be generated through interpolation from first blood pressure data before and after the body movement occurrence period, and second blood pressure data suitable for inference of the respiratory cycle can be obtained.

Advantageous Effects of Invention

According to the present invention, the respiratory cycle of a user can be inferred.

BRIEF DESCRIPTION OF DRAWINGS

FIGS. 5A and 5B are an illustrative diagrams of interpolation processing that is performed by a blood pressure data interpolation unit of FIG. 3.

DESCRIPTION OF EMBODIMENTS

Figure 1:
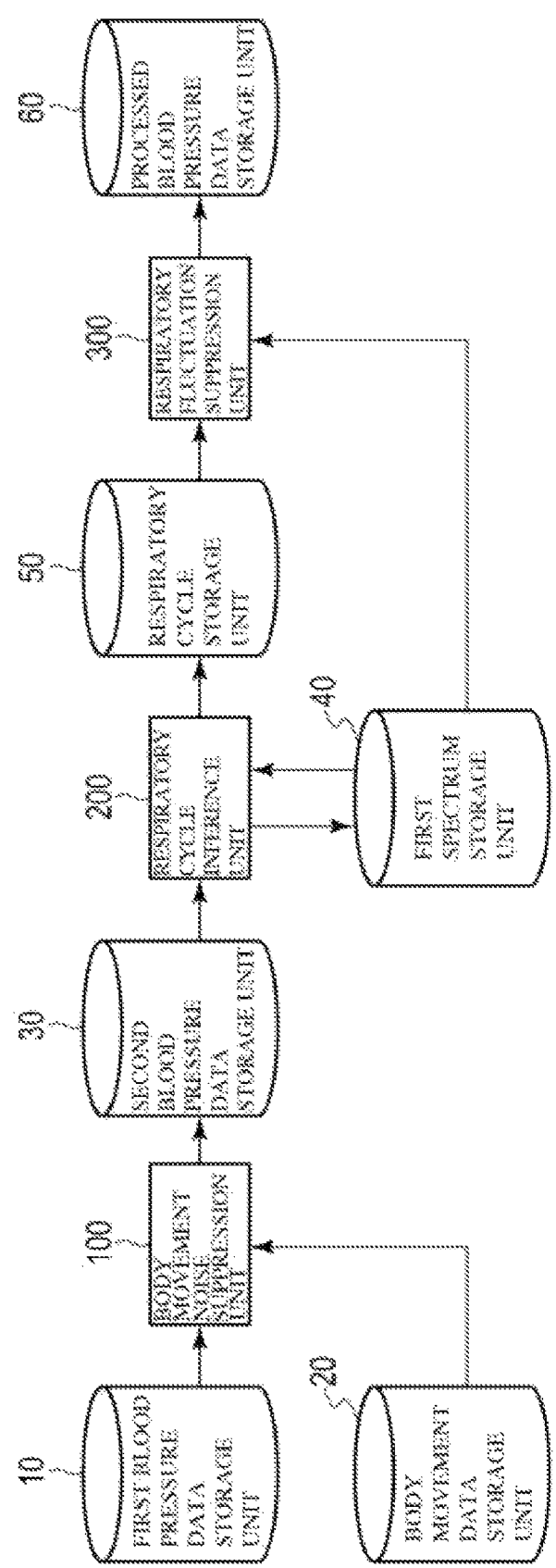
FIG. 1 is a block diagram illustrating a blood pressure data processing apparatus according to a first embodiment.

Hereinafter, description of embodiments will be given with reference to the drawings. Note that, below, the same or similar reference numerals are given to elements that are the same or similar to elements that have already been described, and redundant description will generally be omitted.

First Embodiment

As illustrated in FIG. 1, a blood pressure data processing apparatus according to a first embodiment includes a first blood pressure data storage unit 10, a body movement data storage unit 20, a body movement noise suppression unit 100, a second blood pressure data storage unit 30, a respiratory cycle inference unit 200, a first spectrum storage unit 40, a respiratory cycle storage unit 50, a respiratory fluctuation suppression unit 300, and a processed blood pressure data storage unit 60.

The first blood pressure data storage unit 10 stores blood pressure data (first blood pressure data) obtained by performing measurement (e.g., continuous measurement) of blood pressure with a blood pressure sensor worn by the user. The first blood pressure data stored in the first blood pressure data storage unit 10 is read out by the body movement noise suppression unit 100 as needed.

The first blood pressure data can, for example, include the values of systolic blood pressure and diastolic blood pressure per beat, but is not limited thereto. The first blood pressure data can be associated with respective measurement times.

The blood pressure sensor worn by the user can include a blood pressure sensor (referred to below as "continuous blood pressure sensor") that is capable of continuously measuring the blood pressure of the user per beat. Continuous blood pressure sensors may continuously measure the blood pressure of the user from the pulse transit time (PTT), or may realize continuous measurement by the tonometry method or other techniques.

The blood pressure sensor can, in addition to a continuous blood pressure sensor, also include a blood pressure sensor (referred to below as "discontinuous blood pressure sensor") that is not capable of continuous measurement. Discontinuous blood pressure sensors measure the blood pressure of the user, using a cuff as the pressure sensor (oscillometric method), for example.

Discontinuous blood pressure sensors (particularly blood pressure sensors using the oscillometric method) tend to have high measurement accuracy, compared with continuous blood pressure sensors. Therefore, the blood pressure sensor may, for example, measure blood pressure data with higher accuracy, by operating the discontinuous blood pressure sensor instead of the continuous blood pressure sensor, triggered by some sort of condition being met (e.g., blood pressure data of user measured by the continuous blood pressure sensor indicating a predetermined high risk state).

The body movement data storage unit 20 stores body movement data obtained by measuring motion with a motion sensor worn by the user. The body movement data stored in the body movement data storage unit 20 is read out by the body movement noise suppression unit 100 as needed.

Body movement data can, for example, include the values of one or a plurality of axes of acceleration or angular velocity, but is not limited thereto. Blood pressure data can be associated with respective measurement times. The motion sensor may be an acceleration sensor or an angular velocity sensor, for example. As an example, the motion sensor may be a triaxial acceleration sensor.

The body movement noise suppression unit 100 suppresses noise relating to the body movement of the user included in the first blood pressure data, and generates second blood pressure data. The body movement noise suppression unit 100 saves the second blood pressure data to the second blood pressure data storage unit 30.

Specifically, the body movement noise suppression unit 100 reads out the first blood pressure data from the first blood pressure data storage unit 10, and reads out the body movement data from the body movement data storage unit 20. The body movement noise suppression unit 100 infers a body movement occurrence period based on the body movement data. The body movement noise suppression unit 100 performs data processing on the first blood pressure data associated with the inferred body movement occurrence period, and generates second blood pressure data. The data processing may, for example, be smoothing processing, or may be processing for replacing the first blood pressure data with blood pressure data generated through interpolation.

The second blood pressure data storage unit 30 stores the second blood pressure data generated by the body movement noise suppression unit 100. The second blood pressure data stored in the second blood pressure data storage unit 30 is read out by the respiratory cycle inference unit 200 as needed.

The respiratory cycle inference unit 200 infers the respiratory cycle of the user based on a first spectrum, which is a frequency domain representation of the second blood pressure data, and saves the inferred respiratory cycle to the respiratory cycle storage unit 50.

Specifically, the respiratory cycle inference unit 200 reads out the second blood pressure data from the second blood pressure data storage unit 30, and generates the first spectrum, which is a frequency domain representation thereof. The respiratory cycle inference unit 200 saves the first spectrum to the first spectrum storage unit 40, and calculates the power spectra of the first spectrum. The respiratory cycle inference unit 200 then infers a cycle corresponding to one of the peak frequencies included in the power spectra to be the respiratory cycle of the user, using a technique discussed later.

The respiratory cycle inference unit 200 may, however, not be able to infer the respiratory cycle of the user as will be discussed later. In this case, for example, the respiratory cycle inference unit 200 may perform error processing such as outputting an error screen or an error message from a display device or a speaker that is not illustrated.

The number of second blood pressure data that the respiratory cycle inference unit 200 used in inference of the respiratory cycle of the user can be arbitrarily determined. This number of data may, for example, be designated by the user, who is the person whose blood pressure is to be measured, or another person (e.g., doctor, health instructor or manufacturer, retailer or administrator of blood pressure data processing apparatus), or may be determined automatically.

As an example, the respiratory cycle inference unit 200 may, for example, infer the respiratory cycle of the user from the second blood pressure data for the approximately 7 to 10 hours corresponding to the sleep time of the user at night. Alternatively, the respiratory cycle inference unit 200 may infer the respiratory cycle of the user from the second blood pressure data in a specific time period during the day (e.g., 9:00 PM to 12:00 PM, 1:00 AM to 4:00 AM) or a specific state (e.g., immediately after going to bed, during sleep, immediately before getting out of bed). By narrowing down the number of second blood pressure data that is used in inference of the respiratory cycle in this manner, the respiratory cycle can also be inferred in the case where the respiratory fluctuation of the user is not very stable.

Note that the second blood pressure data may be shaped such that the number of second blood pressure data that are used in inference of the respiratory cycle is a power of two, in order to apply the fast Fourier transform (FFT), as will be discussed later. Therefore, the number of second blood pressure data that the respiratory cycle inference unit 200 reads out from the second blood pressure data storage unit 30 does not need to be made to conform to a power of two.

The first spectrum storage unit 40 stores the first spectrum generated by the respiratory cycle inference unit 200. The first spectrum stored in the first spectrum storage unit 40 is read out by the respiratory cycle inference unit 200 and the respiratory fluctuation suppression unit 300 as needed.

The respiratory cycle storage unit 50 stores the respiratory cycle of the user inferred by the respiratory cycle inference unit 200. The respiratory cycle stored in the respiratory cycle storage unit 50 is read out by the respiratory fluctuation suppression unit 300 as needed.

The respiratory fluctuation suppression unit 300 generates processed blood pressure data in which the respiratory fluctuation of the user included in the second blood pressure data is suppressed, and saves the processed blood pressure data to the processed blood pressure data storage unit 60.

Specifically, the respiratory fluctuation suppression unit 300 reads out the first spectrum from the first spectrum storage unit 40, and reads out the respiratory cycle from the respiratory cycle storage unit 50. The respiratory fluctuation suppression unit 300 suppresses frequency components that correspond to the respiratory cycle within the first spectrum, and then generates processed blood pressure data by transforming the resultant spectrum into a time domain representation.

The processed blood pressure data storage unit 60 stores the processed blood pressure data generated by the respiratory fluctuation suppression unit 300. The processed blood pressure data stored in the processed blood pressure data storage unit 60 may be read out as needed by a functional unit or apparatus for blood pressure data processing which is not illustrated in order to detect sudden fluctuations in blood pressure, for example.

Sudden fluctuations in blood pressure include blood pressure surges. A blood pressure surge refers, for example, to a sudden fluctuation in blood pressure that is triggered by hypoxia in sleep apnea syndrome (SAS) during sleep. Accordingly, monitoring the number of blood pressure surges is useful in ascertaining the severity of symptoms of SAS in the user.

Figure 2:
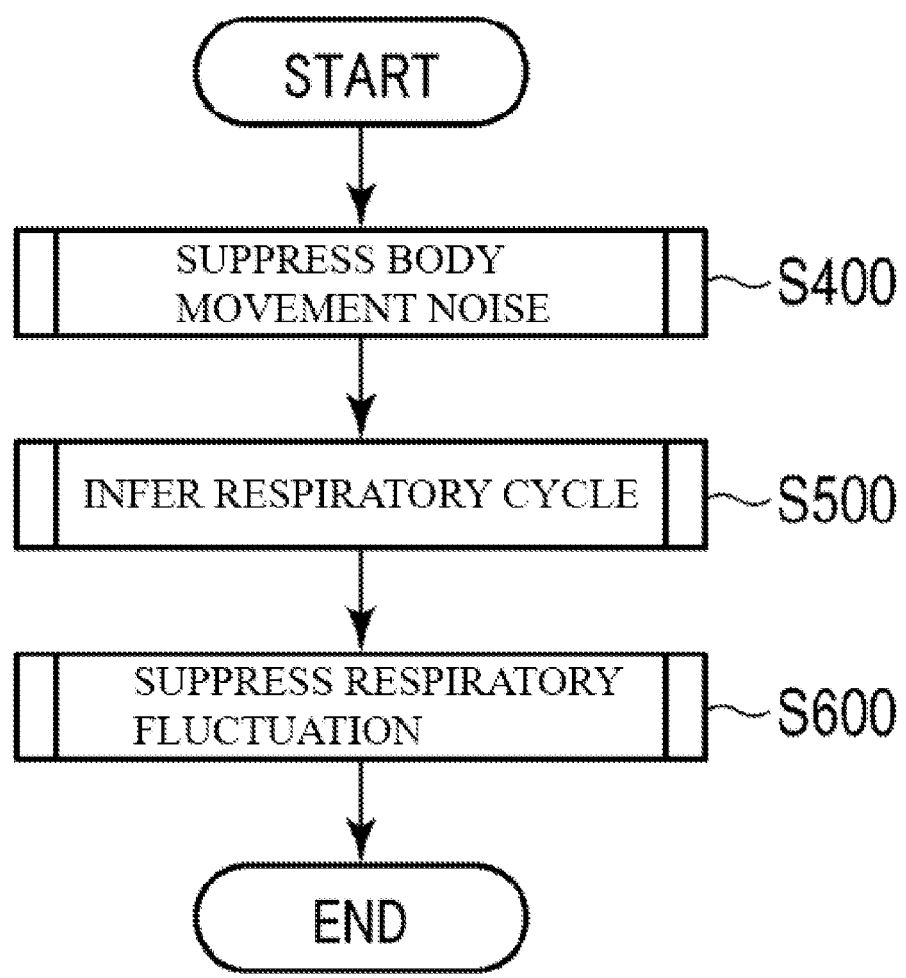
FIG. 2 is a flowchart illustrating operations of the blood pressure data processing apparatus of FIG. 1.

The blood pressure data processing apparatus of FIG. 1 operates as illustrated in FIG. 2.

The body movement noise suppression unit 100 suppresses noise relating to the body movement of the user from the first blood pressure data, and generates second blood pressure data (step S400). Step S400 will be described in detail later using FIG. 4.

The respiratory cycle inference unit 200 infers the respiratory cycle of the user based on a first spectrum, which is a frequency domain representation of the second blood pressure data generated in step S400 (step S500). Step S500 will be described in detail later using FIGS. 8 and 9.

The respiratory fluctuation suppression unit 300 suppresses the respiratory fluctuation of the user included in the second blood pressure data, based on the respiratory cycle of the user inferred in step S500, and generates processed blood pressure data (step S600). Step S600 will be described in detail later using FIG. 13.

Figure 3:
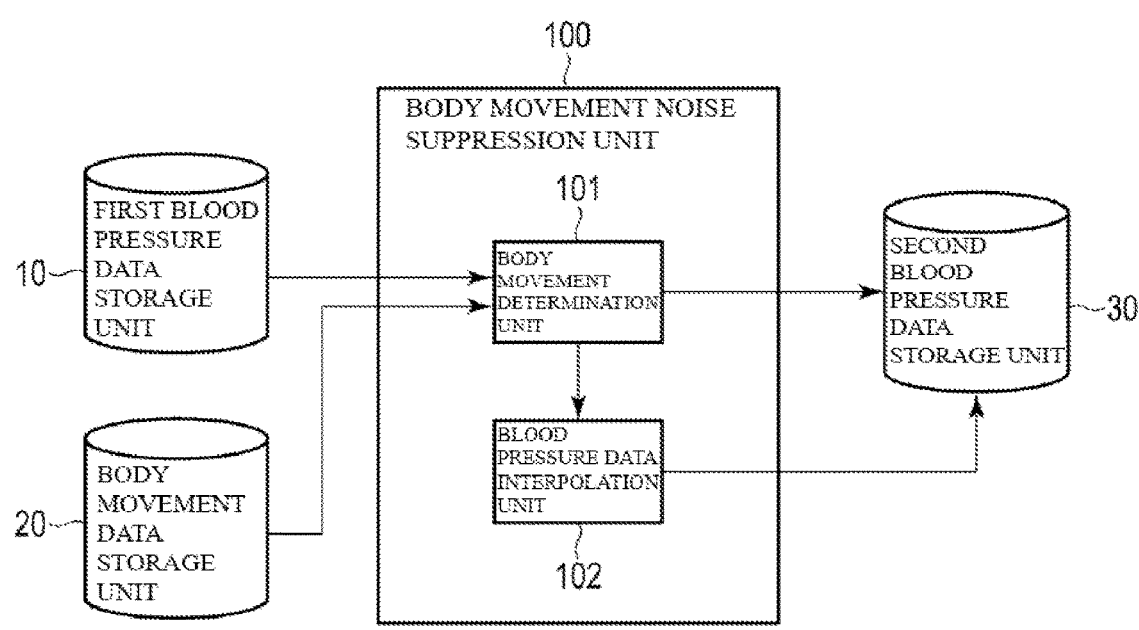
FIG. 3 is a block diagram illustrating a body movement noise suppression unit of FIG. 1 in detail.

The body movement noise suppression unit 100 of FIG. 1 is illustrated in FIG. 3. This body movement noise suppression unit 100 includes a body movement determination unit 101 and a blood pressure data interpolation unit 102.

The body movement determination unit 101 reads out the first blood pressure data from the first blood pressure data storage unit 10, and reads out the body movement data from the body movement data storage unit 20. The body movement determination unit 101 determines, based on body movement data of a unit period, whether body movement has occurred in the unit period. The body movement determination unit 101 saves the first blood pressure data of the unit period to the second blood pressure data storage unit 30 as second blood pressure data of the unit period, if body movement has not occurred in the unit period (pass-through). On the other hand, the body movement determination unit 101 outputs the first blood pressure data of the unit period (below, also referred to as body movement occurrence period) to the blood pressure data interpolation unit 102, if body movement has occurred in the unit period.

Here, the unit period may, for example, be the interval between consecutive beats, that is, one beat cycle (e.g., interval from start point to end point). Alternatively, the unit period may be a plurality of connected intervals, that is, a plurality of beat cycles. Processing for suppressing body movement noise can thereby be performed per beat.

The blood pressure data interpolation unit 102 receives the first blood pressure data of a body movement occurrence period from the body movement determination unit 101. The blood pressure data interpolation unit 102 generates blood pressure data through interpolation to replace this first blood pressure data from the first blood pressure data before and after the body movement occurrence period. An interpolation method such as linear interpolation or spline interpolation, for example, may be used in generating blood pressure data through interpolation. According to this interpolation processing, unreliable blood pressure data can be discarded and pseudo blood pressure data generated utilizing time correlation of blood pressure data can be utilized. The blood pressure data interpolation unit 102 then saves the blood pressure data generated through interpolation to the second blood pressure data storage unit 30 as the second blood pressure data of the body movement occurrence period. Note that a data processing unit that performs other noise reduction processing such as smoothing, for example, may be provided instead of the blood pressure data interpolation unit 102 or in addition to the blood pressure data interpolation unit 102.

In FIG. 5, (first) blood pressure data and acceleration data serving as body movement data are illustrated. Assume that the body movement determination unit 101 has determined that body movement has occurred in the period shown in FIG. 5. In this case, the blood pressure data interpolation unit 102 can replace the blood pressure data of the body movement occurrence period with blood pressure data generated through interpolation based on the blood pressure data before and after that period, and generate the (second) blood pressure data illustrated in FIG. 6. Note that, in the example in FIG. 6, the blood pressure data interpolation unit 102 targets systolic blood pressure for processing, but does not target diastolic blood pressure for processing. However, the blood pressure data interpolation unit 102 may further process diastolic blood pressure.

Figure 6:
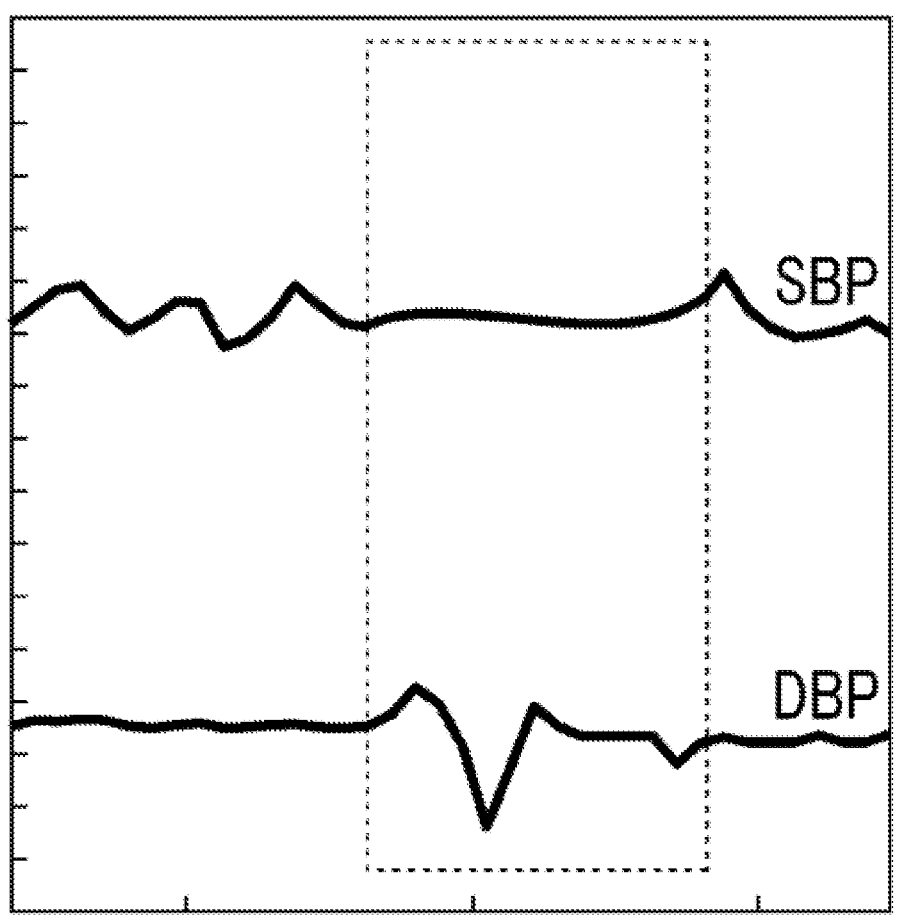
FIG. 6 is an illustrative diagram of interpolation processing that is performed by the blood pressure data interpolation unit of FIG. 3.

In the example in FIGS. 5 and 6, the waveforms for only systolic blood pressure (SBP) and diastolic blood pressure (DBP) are depicted as blood pressure data for simplification, but in the case where pressure pulse wave data per beat is measured by a continuous blood pressure sensor worn by the user, it is also possible to visualize the waveform of this pressure pulse wave.

Figure 4:
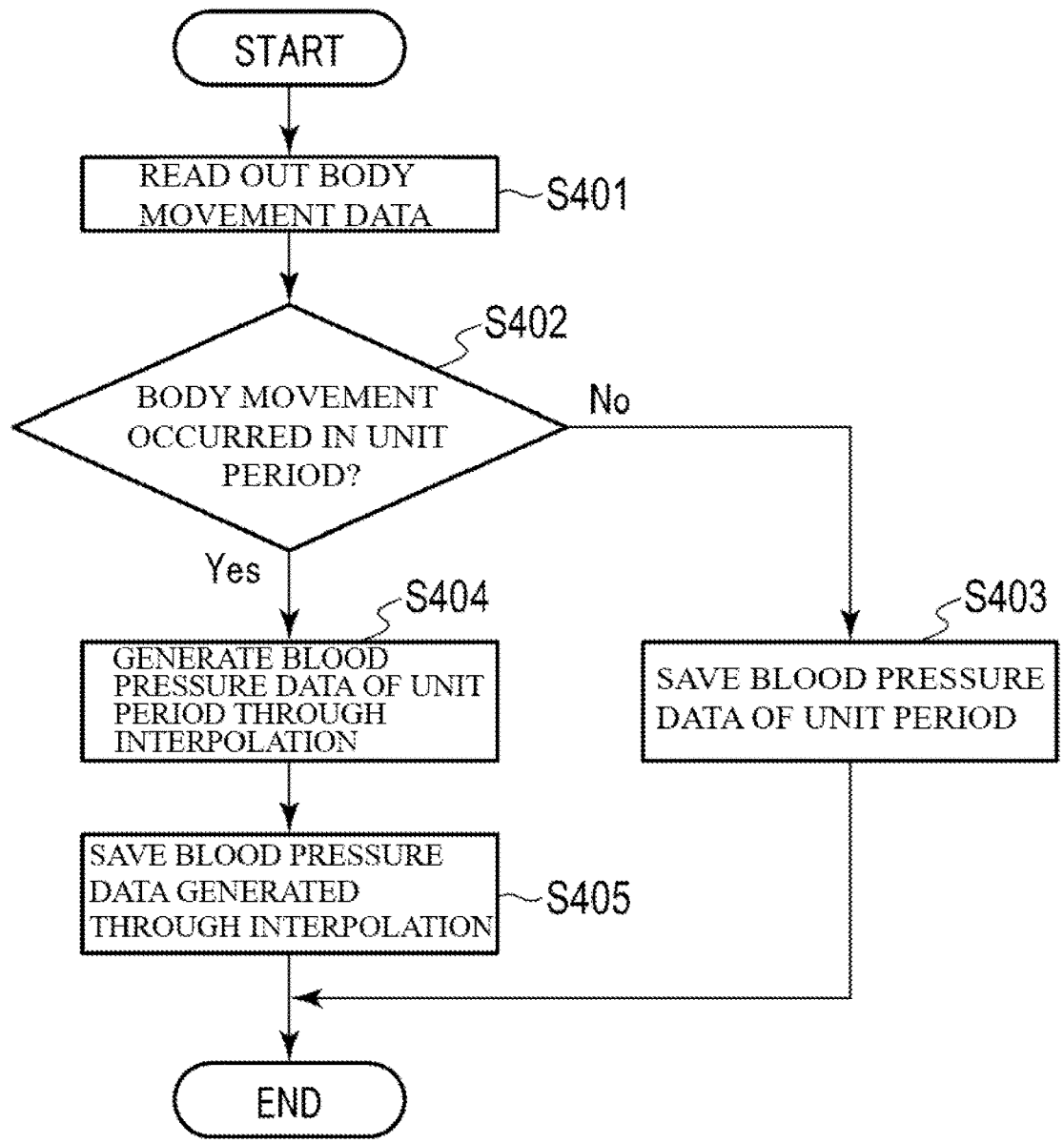
FIG. 4 is a flowchart illustrating step S400 of FIG. 2 in detail.

Step S400 of FIG. 2 is illustrated in detail in FIG. 4.

The body movement determination unit 101 reads out the body movement data of the unit period from the body movement data storage unit 20 (step S401). The body movement determination unit 101 determines whether body movement has occurred in the unit period that is associated with the body movement data, based on the body movement data read out in step S401 (step S402). If it is determined that body movement has occurred, the processing advances to step S404, and if this is not the case, the processing advances to step S403.

In step S403, the body movement determination unit 101 saves the first blood pressure data of the unit period with respect to which it was determined in step S402 that body movement has not occurred to the second blood pressure data storage unit 30.

In step S404, the blood pressure data interpolation unit 102 generates blood pressure data through interpolation to replace the first blood pressure data for the unit period with respect to which it was determined in step S402 that body movement has occurred. Then, the blood pressure data interpolation unit 102 saves the blood pressure data generated through interpolation in step S404 to the second blood pressure data storage unit 30 (step S405).

Figure 7:
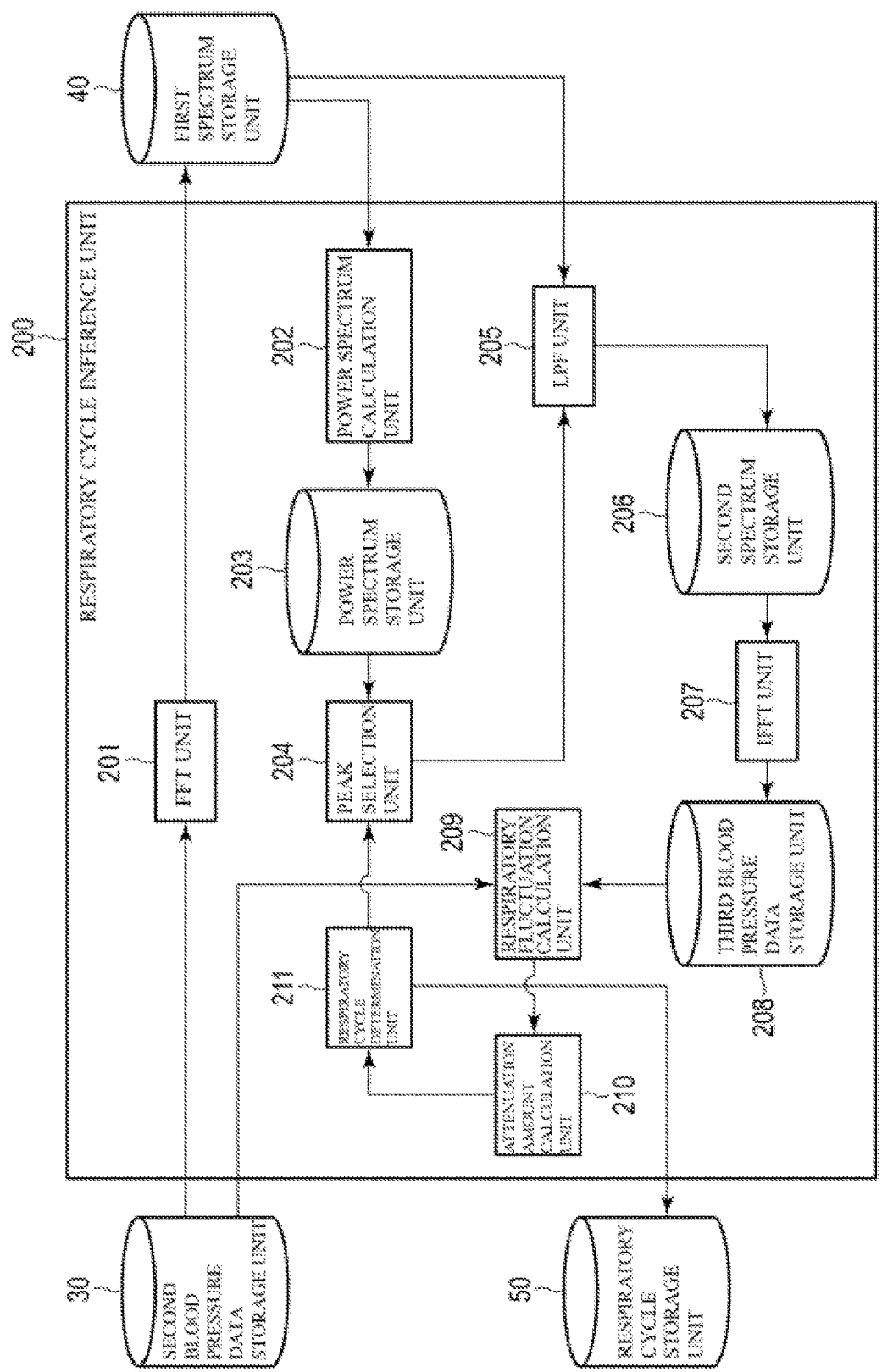
FIG. 7 is a block diagram illustrating a respiratory cycle inference unit of FIG. 1 in detail.

The respiratory cycle inference unit 200 of FIG. 1 is illustrated in detail in FIG. 7. This respiratory cycle inference unit 200 includes an FFT unit 201, a power spectrum calculation unit 202, a power spectrum storage unit 203, a peak selection unit 204, a low pass filter (LPF) unit 205, a second spectrum storage unit 206, an IFFT (Inverse FFT) unit 207, a third blood pressure data storage unit 208, a respiratory fluctuation calculation unit 209, an attenuation amount calculation unit 210, and a respiratory cycle determination unit 211.

The FFT unit 201 reads out the second blood pressure data from the second blood pressure data storage unit 30. The FFT unit 201 performs FFT on the second blood pressure data, and generates a first spectrum, which is a frequency domain representation of the second blood pressure data. The FFT unit 201 saves the first spectrum to the first spectrum storage unit 40. Note that the FFT unit 201 may shape the second blood pressure data before performing FFT, such that the number of second blood pressure data is a power of two. The FFT unit 201 may be replaced by another time-frequency transformation unit.

The power spectrum calculation unit 202 reads out the first spectrum from the first spectrum storage unit 40. The power spectrum calculation unit 202 calculates the power spectra of the first spectrum. The power spectrum calculation unit 202 saves the power spectra to the power spectrum storage unit 203.

The power spectrum storage unit 203 stores the power spectra calculated by the power spectrum calculation unit 202. The power spectra stored in the power spectrum storage unit 203 are read out by the peak selection unit 204 as needed.

The peak selection unit 204 reads out the power spectra from the power spectrum storage unit 203. The peak selection unit 204 selects one of the peak frequencies indicating peaks in the power spectra. The peak selection unit 204 notifies the selected peak to the LPF unit 205.

Verification of whether the peak frequency that is selected by the peak selection unit 204 corresponds to the respiratory frequency is performed by the respiratory cycle determination unit 211 discussed later. In the case where the peak frequency that is selected does not correspond to the respiratory frequency of the user, the respiratory cycle determination unit 211 then causes the peak selection unit 204 to select one of the unselected peak frequencies. If the search for the peak frequency corresponding to the respiratory cycle is performed in this way, the respiratory cycle can be stably and accurately inferred regardless of factors such as the personal traits or the mental or physical state of the user, or the environment in which blood pressure is measured.

Figure 10:
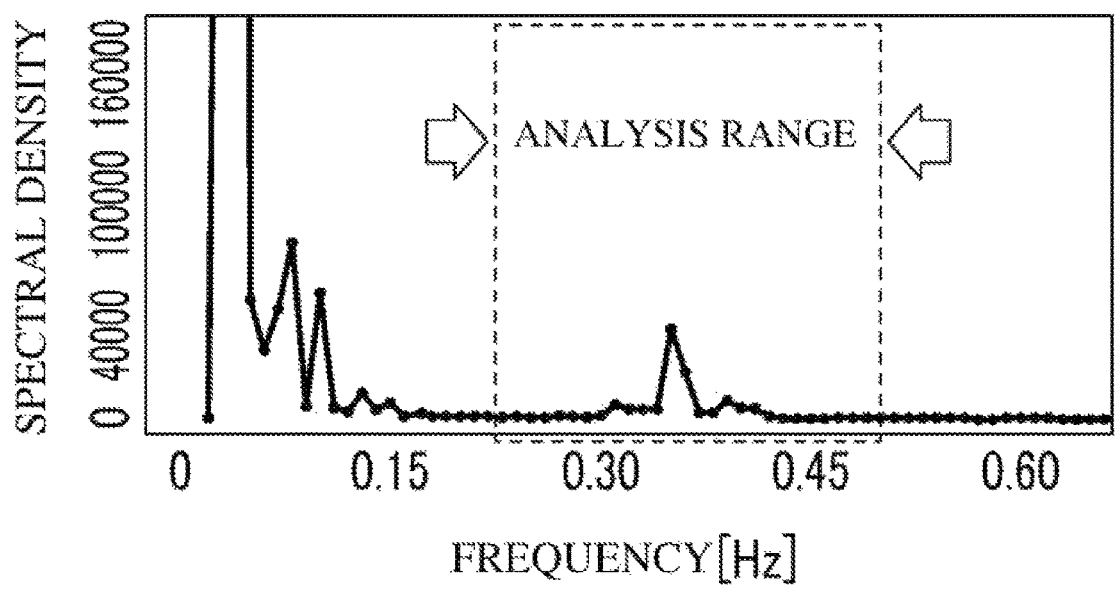
FIG. 10 is a diagram illustrating an analysis range over which a peak frequency can be selected by a peak selection unit of FIG. 7.

Specifically, the peak selection unit 204 may set a narrower analysis range than all the frequency bands of the power spectra, and select one of the peak frequencies from this analysis range. An example of the analysis range is shown in FIG. 10. The analysis range may be set a high frequency domain compared with the frequency domain over which the main blood pressure fluctuation components of the user are distributed. The analysis range can be determined in a range in which the respiratory frequency corresponding to the respiratory cycle of the user is likely to exist. For example, the analysis range may be determined based on measurement of the distribution of the respiratory frequency of the user who is targeted for inference of the respiratory cycle or another user, or may be determined theoretically.

Figure 11:
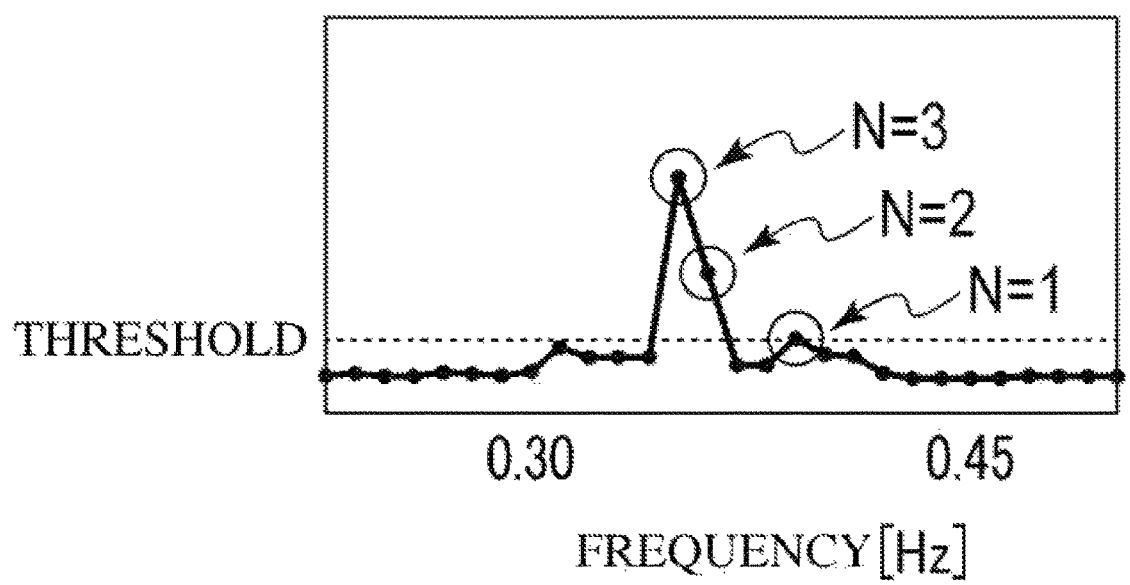
FIG. 11 is an illustrative diagram of operations of the peak selection unit of FIG. 7.

The peak selection unit 204 may, furthermore, set a threshold, and make a selection limited to peak frequencies indicating a peak that is greater than or equal to this threshold. The threshold is, for example, the average value of power spectra within the analysis range, but is not limited thereto. The peak selection unit 204 may, furthermore, select peak frequencies in descending order of frequency, as illustrated in FIG. 11. In the example in FIG. 11, N represents the selection order of peak frequencies, and the peak selection unit 204 initially selects the peak frequency N=1. Generally, the respiratory frequency is in a high frequency domain compared with the frequency domain over which the main blood pressure fluctuation components of the user are distributed. Therefore, the search for the peak frequency corresponding to the respiratory cycle can be conducted efficiently, and an erroneous respiratory cycle being inferred due to the blood pressure fluctuation components of the user can be prevented.

The LPF unit 205 reads out the first spectrum from the first spectrum storage unit 40, and receives notification of the peak frequency that is selected from the peak selection unit 204. The LPF unit 205 performs low pass filtering on the first spectrum to generate a second spectrum. The cutoff frequency of this low pass filtering is set to lower than the selected peak frequency. That is, this peak frequency is not included in the passband. High frequency components that include the components of the peak frequency within the first spectrum can thereby be collectively suppressed. The LPF unit 205 saves the second spectrum to the second spectrum storage unit 206.

Note that the LPF unit 205 may be replaced by a frequency component suppression unit that suppresses the components of the selected peak frequency within the first spectrum and generates a second spectrum. This frequency component suppression unit may, for example, perform band-reject filtering that includes this peak frequency in the stop band.

The second spectrum storage unit 206 stores the second spectrum generated by the LPF unit 205. The second spectrum stored in the second spectrum storage unit 206 is read out by the IFFT unit 207 as needed.

The IFFT unit 207 reads out the second spectrum from the second spectrum storage unit 206. The IFFT unit 207 performs IFFT on the second spectrum and generates third blood pressure data, which is a time domain representation of the second spectrum. The IFFT unit 207 saves the third blood pressure data to the third blood pressure data storage unit 208. The IFFT unit 207 may be replaced by another frequency-time transformation unit.

The third blood pressure data storage unit 208 stores the third blood pressure data generated by the respiratory fluctuation calculation unit 209. The third blood pressure data stored in the third blood pressure data storage unit 208 is read out by the respiratory fluctuation calculation unit 209 as needed.

The respiratory fluctuation calculation unit 209 reads out the second blood pressure data from the second blood pressure data storage unit 30, and reads out the third blood pressure data from the third blood pressure data storage unit 208. The respiratory fluctuation calculation unit 209 calculates both the respiratory fluctuation (referred to as "first respiratory fluctuation") in the second blood pressure data and the respiratory fluctuation (referred to as "second respiratory fluctuation") in the third blood pressure data. The respiratory fluctuation calculation unit 209 outputs the first respiratory fluctuation and the second respiratory fluctuation to the attenuation amount calculation unit 210.

The attenuation amount calculation unit 210 calculates the attenuation amount of the second respiratory fluctuation relative to the first respiratory fluctuation. If the frequency components that correspond to the respiratory cycle are suppressed by the LPF unit 205, the second respiratory fluctuation will be greatly attenuated relative to the first respiratory fluctuation. That is, it becomes possible to infer that the cycle corresponding to the peak frequency that is selected by the peak selection unit 204 is the respiratory cycle. The attenuation amount calculation unit 210 notifies the attenuation amount to the respiratory cycle determination unit 211.

The respiratory cycle determination unit 211 receives notification of the attenuation amount from the attenuation amount calculation unit 210. The respiratory cycle determination unit 211 compares the attenuation amount with a threshold Y. If the attenuation amount is greater than the threshold Y, the respiratory cycle determination unit 211 determines the cycle corresponding to the peak frequency that is selected by the peak selection unit 204 as the respiratory cycle of the user. Then, the peak selection unit 204 saves the respiratory cycle of the user to the respiratory cycle storage unit 50. On the other hand, if the attenuation amount is less than or equal to the threshold Y, the respiratory cycle determination unit 211 causes the peak selection unit 204 to select one of the unselected peak frequencies.

The peak selection unit 204 may, however, restrict the available number of peak frequency selections. Specifically, the peak selection unit 204 may, even in the case where unselected peak frequencies remain, perform error processing (e.g., output of an error screen or error message indicating that the respiratory cycle cannot be inferred), assuming that the respiratory cycle cannot be inferred, if the number of peak frequency selections has reached the available number of selections. Similar processing is also performed in the case where no unselected peak frequencies remain.

In the case where the respiratory cycle cannot be inferred, the respiratory cycle may be inferred again, after changing (e.g., narrowing down) the number of second blood pressure data that are used in inference of the respiratory cycle or performing different body movement noise suppression processing in the body movement noise suppression unit 100 and regenerating the second blood pressure data, for example.

Figure 8:
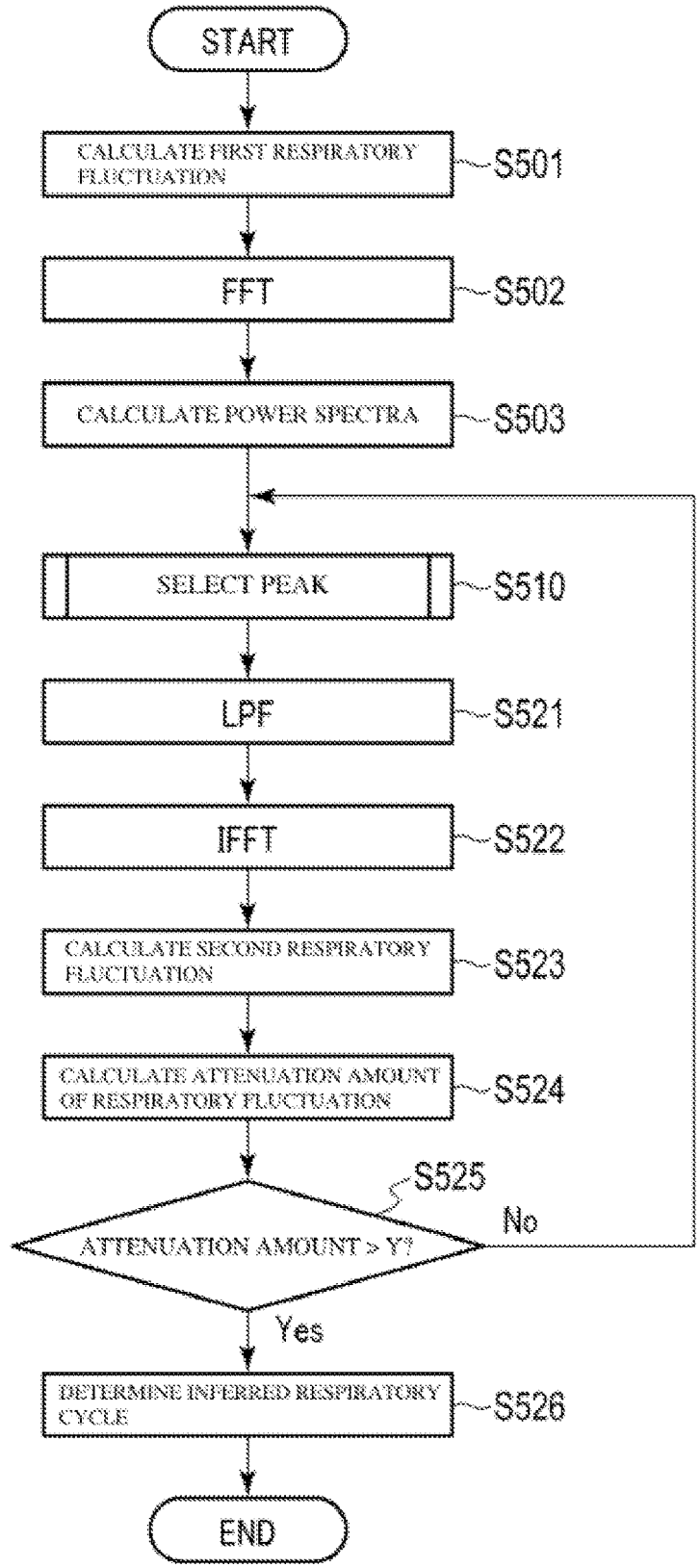
FIG. 8 is a flowchart illustrating step S500 of FIG. 2 in detail.

Step S500 of FIG. 2 is illustrated in detail in FIG. 8.

The respiratory fluctuation calculation unit 209 calculates the first respiratory fluctuation in the second blood pressure data generated in step S400 (step S501). On the other hand, the FFT unit 201 performs FFT on the second blood pressure data generated in step S400 and generates a first spectrum (step S502). Note that steps S501 and S502 can be executed in a different order to FIG. 8.

The power spectrum calculation unit 202 calculates the power spectra of the first spectrum generated in step S502 (step S503). After step S503, the processing advances to step S510.

In step S510, the peak selection unit 204 selects one of the peak frequencies from the power spectra calculated in step S503. Note that step S510 will be discussed in detail later using FIG. 9.

The LPF unit 205 performs low pass filtering in which the cutoff frequency is set to lower than the peak frequency selected in step S510 on the first spectrum generated in step S502, and generates a second spectrum (step S521). The IFFT unit 207 performs IFFT on the second spectrum generated in step S521, and generates third blood pressure data (step S522).

The respiratory fluctuation calculation unit 209 calculates the second respiratory fluctuation in the third blood pressure data generated in step S522 (step S523). The attenuation amount calculation unit 210 calculates the attenuation amount of the second respiratory fluctuation calculated in step S523 relative to the first respiratory fluctuation calculated in step S501 (step S524).

The respiratory cycle determination unit 211 compares the attenuation amount calculated in step S524 with the threshold Y (step S525). If the attenuation amount is greater than the threshold Y, the respiratory cycle determination unit 211 determines the cycle corresponding to the peak frequency selected in step S510 as the respiratory cycle of the user (step S526). On the other hand, if the attenuation amount is less than or equal to the threshold Y, the processing returns to step S510. As a result, the peak selection unit 204 will select one of the unselected peak frequencies.

Figure 9:
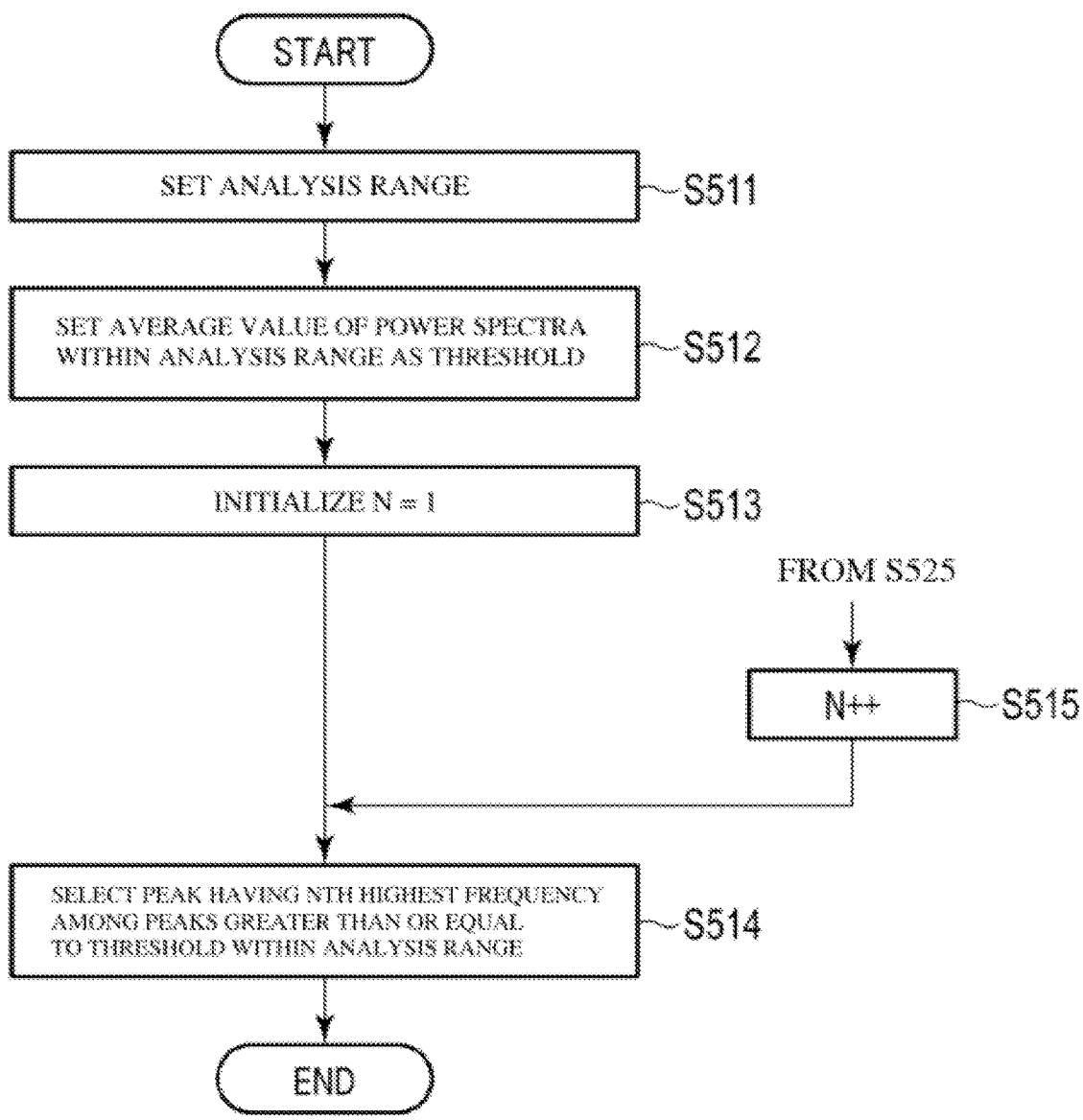
FIG. 9 is a flowchart illustrating step S510 of FIG. 8 in detail.

Step S510 of FIG. 8 is illustrated in detail in FIG. 9.

After step S503 of FIG. 8, the peak selection unit 204 sets an analysis range narrower than all the frequency bands of the power spectra (step S511). The peak selection unit 204 calculates the average value of the power spectra (calculated in step S503 of FIG. 8) of the analysis range set in step S511, and sets a threshold so as to approximately conform to this average value (step S512). The peak selection unit 204 initializes the variable N to 1, and the processing advances to step S514.

In step S514, the peak selection unit 204 selects the peak frequency having the Nth highest frequency among the peak frequencies indicating a peak greater than or equal to the threshold set in step S512 within the analysis range set in step S511, and the processing advances to step S521 of FIG. 8.

Note that in the case where the processing returns from step S525 to step S510, the peak selection unit 204 increments the variable N by 1 (step S515), and the processing advances to step S514.

Note that the processing of FIG. 9 may be partially modified. Specifically, a determination step may be further provided between steps S515 and S514. In this determination step, it is determined whether N is less than or equal to a predetermined available number of selections. If N is less than or equal to the available number of selections, the processing advances to step S514. On the other hand, if N exceeds the available number of selections, the processing ends after predetermined error processing (e.g., output of an error screen or error message indicating that the respiratory cycle cannot be inferred).

Figure 12:
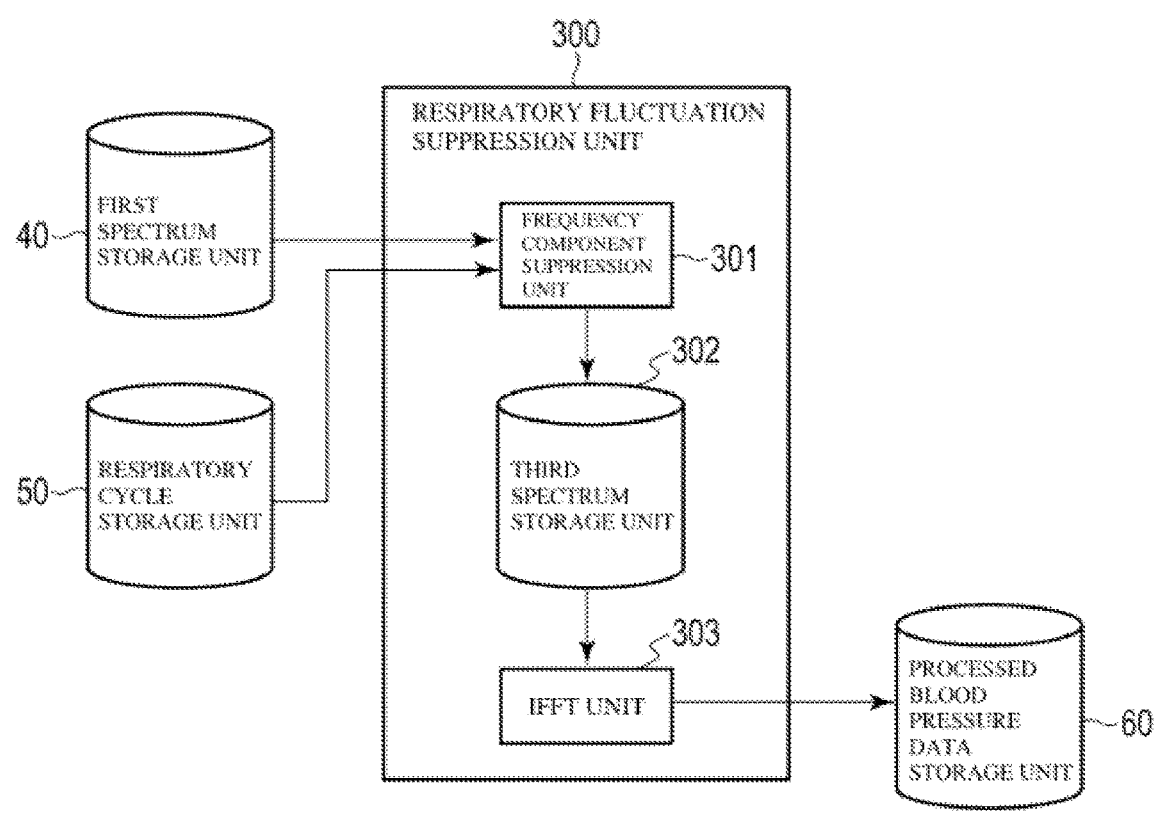
FIG. 12 is a block diagram illustrating a respiratory fluctuation suppression unit of FIG. 1 in detail.

The respiratory fluctuation suppression unit 300 of FIG. 1 is illustrated in detail in FIG. 12. This respiratory fluctuation suppression unit 300 includes a frequency component suppression unit 301, a third spectrum storage unit 302 and an IFFT unit 303.

The frequency component suppression unit 301 reads out the first spectrum from the first spectrum storage unit 40, and reads out the respiratory cycle of the user from the respiratory cycle storage unit 50. The frequency component suppression unit 301 suppresses the frequency components that correspond to the respiratory cycle of the user within the first spectrum, and generates a third spectrum. The frequency component suppression unit 301 saves the third spectrum to the third spectrum storage unit 302.

Figure 14:
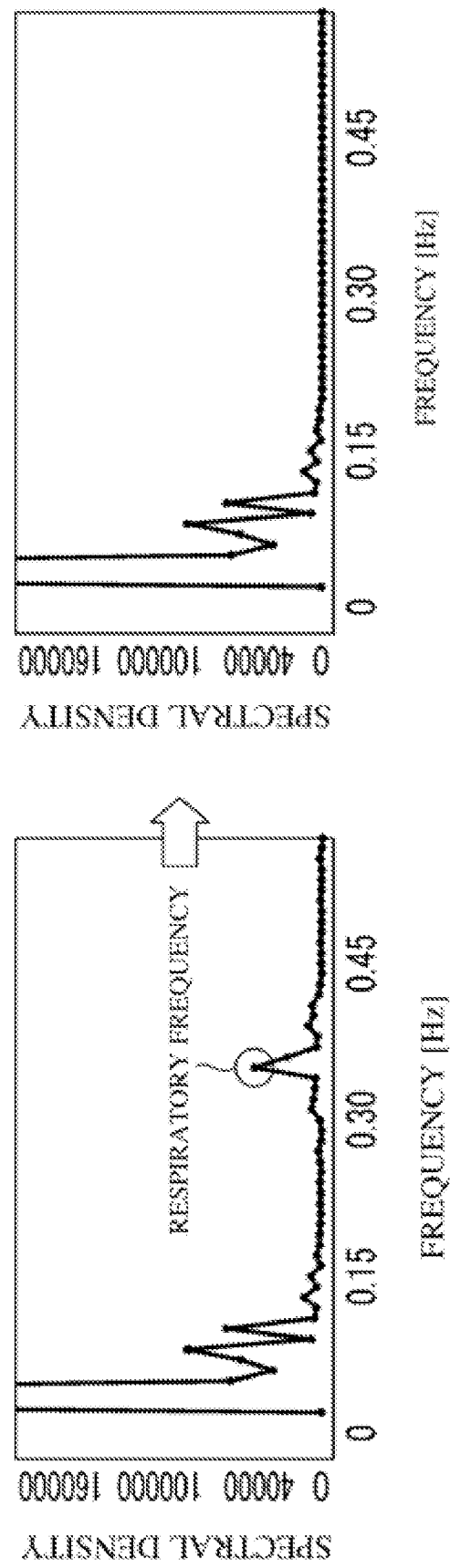
FIG. 14 is an illustrative diagram of operations of a frequency component suppression unit of FIG. 12.

The frequency component suppression unit 301 may, for example, perform low pass filtering in which the cutoff frequency is set to lower than the respiratory frequency corresponding to the respiratory cycle of the user or band-reject filtering that includes the respiratory frequency in the stop band. The components of the respiratory frequency of the user will thereby be suppressed, as illustrated in FIG. 14.

The third spectrum storage unit 302 stores the third spectrum generated by the frequency component suppression unit 301. The third spectrum stored in the third spectrum storage unit 302 is read out by the IFFT unit 303 as needed.

The IFFT unit 303 reads out the third spectrum from the third spectrum storage unit 302. The IFFT unit 303 performs IFFT on the third spectrum, and generates processed blood pressure data, which is a time domain representation of the third spectrum. The IFFT unit 303 saves the processed blood pressure data to the processed blood pressure data storage unit 60. The IFFT unit 303 may be replaced by another frequency-time transformation unit.

Figure 15:
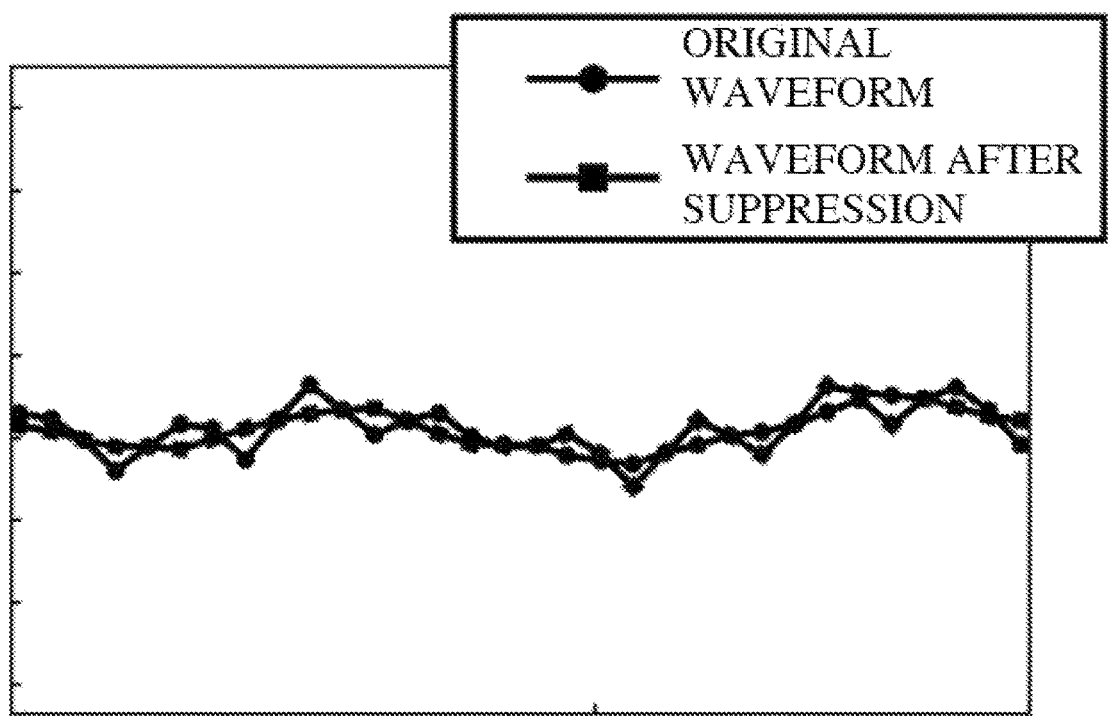
FIG. 15 is a graph illustrating the waveform (original waveform) of second blood pressure data and the waveform (waveform after respiratory fluctuation suppression) of processed blood pressure data.

FIG. 15 illustrates the waveform (original waveform) of the second blood pressure data and the waveform (waveform after respiratory fluctuation suppression) of the processed blood pressure data. Note that the second blood pressure data and processed blood pressure data of FIG. 15 correspond to the power spectra illustrated in FIG. 14. Because cyclic vibration due to respiratory fluctuation has been suppressed in the processed blood pressure data, this data is suitable for analysis of blood pressure fluctuations (e.g., blood pressure surges) caused by factors other than the user's breathing.

Figure 13:
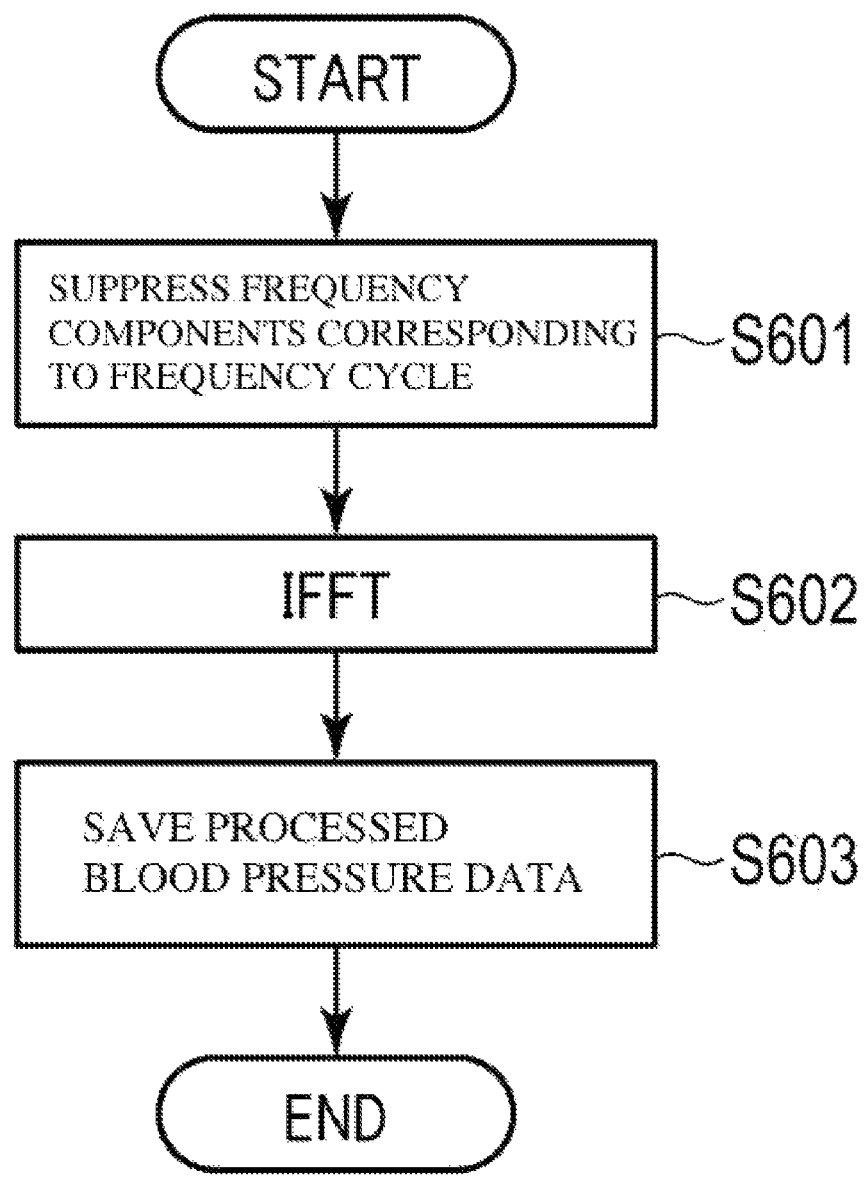
FIG. 13 is a flowchart illustrating step S600 of FIG. 2 in detail.

Step S600 of FIG. 2 is illustrated in detail in FIG. 13.

The frequency component suppression unit 301 suppresses the frequency components that correspond to the respiratory cycle of the user inferred in step S500 of FIG. 2 within the first spectrum, and generates a third spectrum (step S601).

The IFFT unit 303 performs IFFT on the third spectrum generated in step S601, and generates processed blood pressure data, which is a time domain representation of the third spectrum (step S602). The IFFT unit 303 saves the processed blood pressure data generated in step S602 to the processed blood pressure data storage unit 60 (step S603).

As described above, the blood pressure data processing apparatus according to the first embodiment infers the respiratory cycle of the user based on a spectrum that is a frequency domain representation of blood pressure data in which noise relating to the body movement of the user is suppressed. Specifically, the blood pressure data processing apparatus selects one of the peak frequencies indicating a peak in the power spectra of this spectrum, and verifies, based on the attenuation amount of the respiratory fluctuation in the case where the components of the peak frequency are suppressed, whether this peak frequency corresponds to the respiratory frequency. Therefore, according to this blood pressure data processing apparatus, the respiratory cycle can be stably and accurately inferred regardless of factors such as the personal traits or the mental or physical state of the user, whether or not there is body movement, or the environment in which blood pressure is measured.

Also, this blood pressure data processing apparatus generates processed blood pressure data in which the respiratory fluctuation of the user is suppressed, using the inferred respiratory cycle. Therefore, according to this blood pressure data processing apparatus, processed blood pressure data suitable for analysis of blood pressure fluctuations (e.g., blood pressure surges) caused by factors other than the user's breathing can be obtained. That is, as aforementioned, the respiratory cycle can be correctly inferred from the power spectra shown in FIG. 14, and the processed blood pressure data shown in FIG. 15 can be generated.

Figure 16:
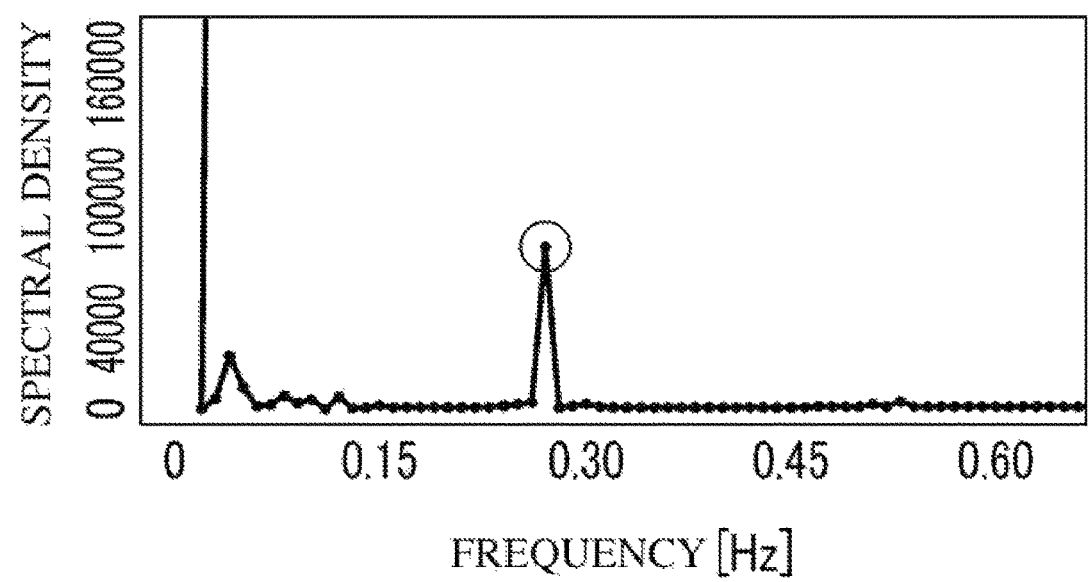
FIG. 16 is a diagram illustrating power spectra in the case where the respiratory frequency is in a different position from FIG. 14.
Figure 17:
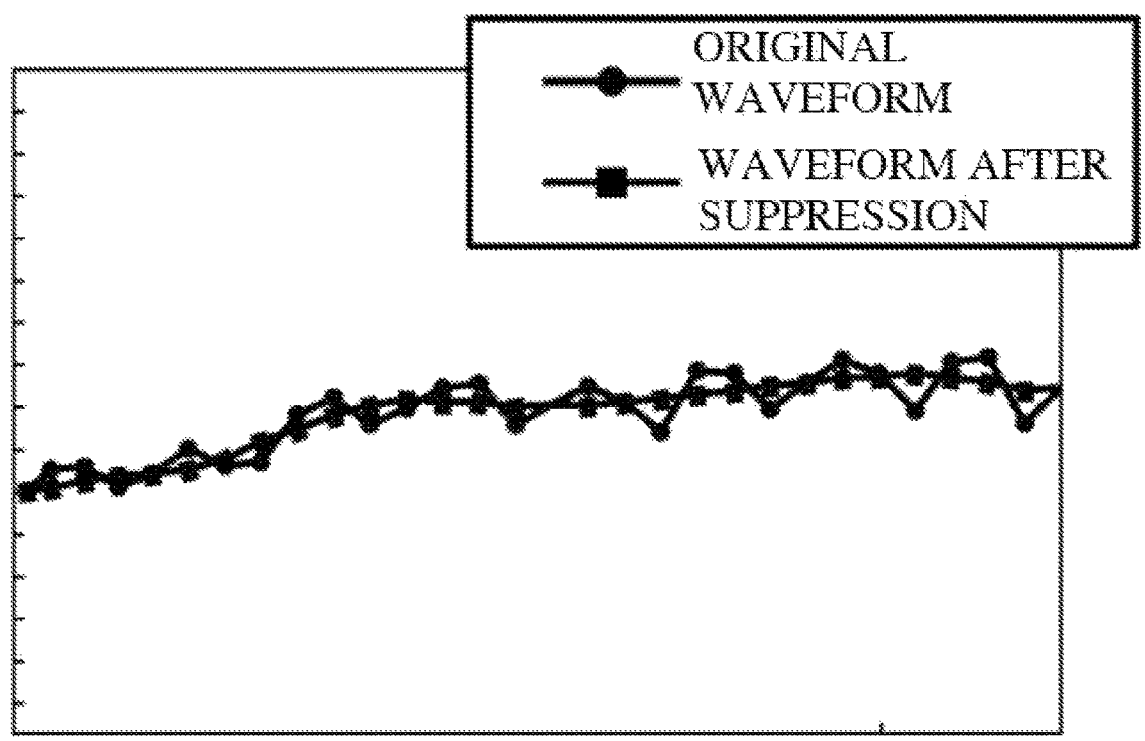
FIG. 17 is a graph illustrating the waveform (original waveform) of second blood pressure data and the waveform (waveform after respiratory fluctuation suppression) of processed blood pressure data.

Furthermore, as aforementioned, according to this blood pressure data processing apparatus, the respiratory cycle can be stably and accurately inferred regardless of factors such as the personal traits or the mental or physical state of the user, whether or not there is body movement, or the environment in which blood pressure is measured. FIG. 16 illustrates power spectra in which the respiratory frequency is in a different position to FIG. 14. This blood pressure data processing apparatus is also able to correctly infer the respiratory cycle and generate the processed blood pressure data illustrated in FIG. 17 in the case where these power spectra are obtained.

Second Embodiment

Figure 18:
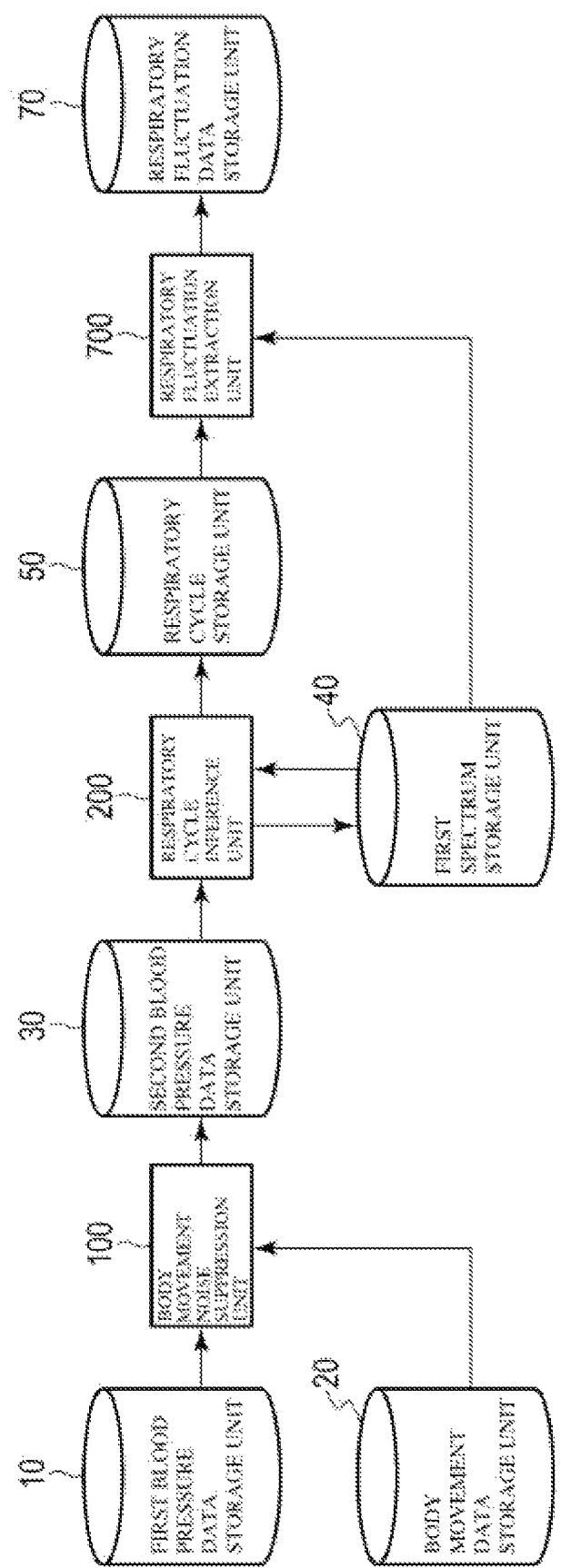
FIG. 18 is a block diagram illustrating a blood pressure data processing apparatus according to a second embodiment.

As illustrated in FIG. 18, the blood pressure data processing apparatus according to a second embodiment includes a first blood pressure data storage unit 10, a body movement data storage unit 20, a body movement noise suppression unit 100, a second blood pressure data storage unit 30, a respiratory cycle inference unit 200, a first spectrum storage unit 40, a respiratory cycle storage unit 50, a respiratory fluctuation extraction unit 700, and a respiratory fluctuation data storage unit 70.

The respiratory fluctuation extraction unit 700 extracts the respiratory fluctuation of the user included in second blood pressure data to generate respiratory fluctuation data, and saves the generated respiratory fluctuation data to the respiratory fluctuation data storage unit 70.

Specifically, the respiratory fluctuation extraction unit 700 reads out the first spectrum from the first spectrum storage unit 40, and reads out the respiratory cycle from the respiratory cycle storage unit 50. The respiratory fluctuation extraction unit 700 suppresses frequency components that do not correspond to the respiratory cycle within the first spectrum, and then generates the respiratory fluctuation data by transforming the resultant spectrum into a time domain representation.

The respiratory fluctuation data storage unit 70 stores the respiratory fluctuation data generated by the respiratory fluctuation extraction unit 700. The respiratory fluctuation data stored in the respiratory fluctuation data storage unit 70 may be read out as needed by a functional unit or apparatus for blood pressure data processing that is not illustrated in order to detect pulsus *paradoxus*, for example. Monitoring pulsus *paradoxus* is useful in ascertaining the severity of symptoms of disorders such as asthma, COPD and cardiac tamponade in the user.

Figure 19:
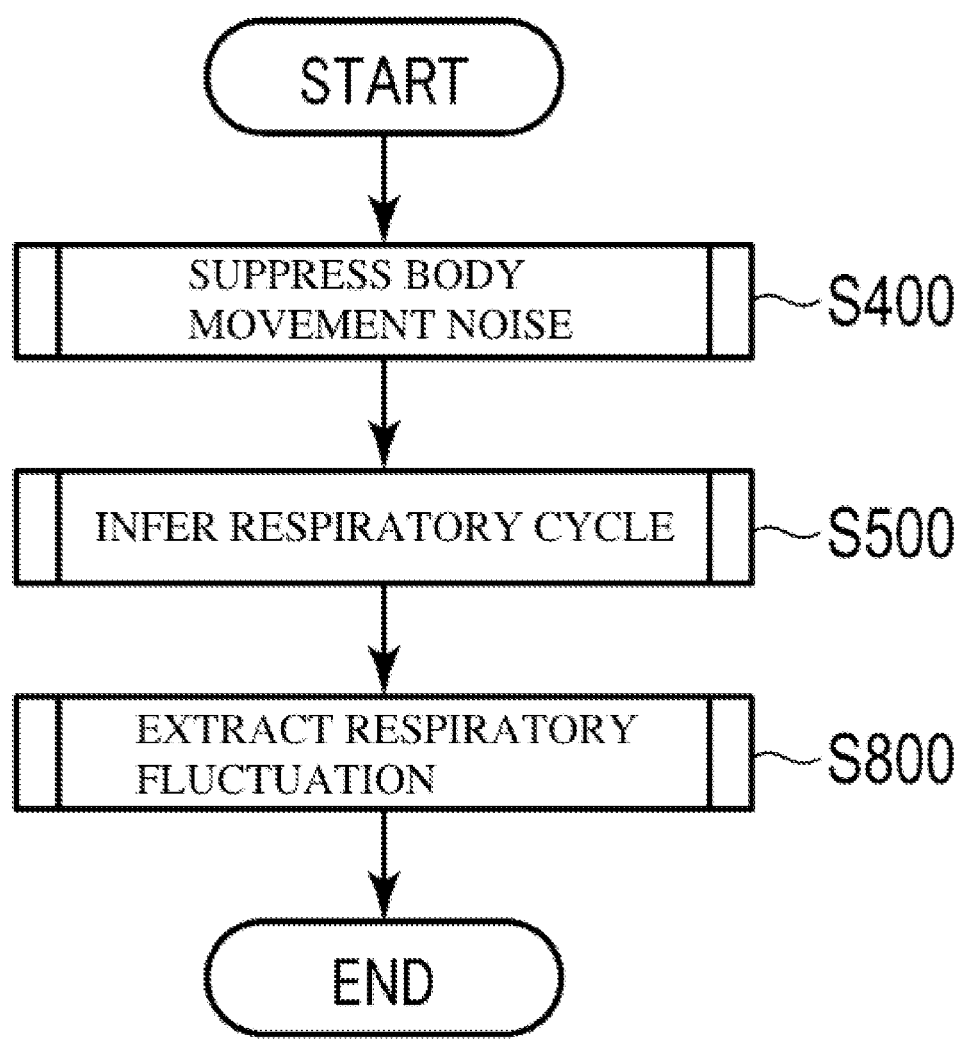
FIG. 19 is a flowchart illustrating operations of the blood pressure data processing apparatus of FIG. 18.

The blood pressure data processing apparatus of FIG. 18 operates as illustrated in FIG. 19. In FIG. 19, steps S400 and S500 can be similar to FIG. 2.

The respiratory fluctuation extraction unit 700 extracts the respiratory fluctuation of the user included in the second blood pressure data, based on the respiratory cycle of the user inferred in step S500, and generates respiratory fluctuation data (step S800). Step S800 will be described in detail later using FIG. 21.

Figure 20:
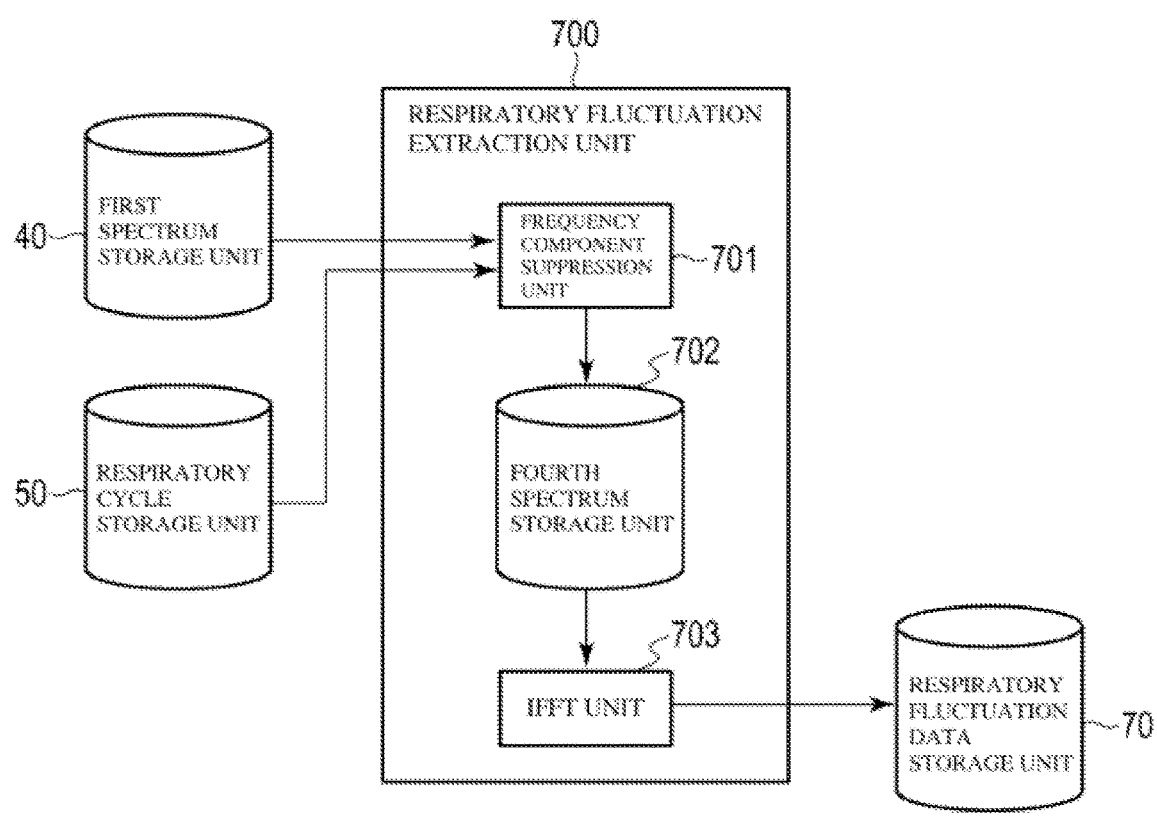
FIG. 20 is a block diagram illustrating a respiratory fluctuation extraction unit of FIG. 18 in detail.

The respiratory fluctuation extraction unit 700 of FIG. 18 is illustrated in detail in FIG. 20. This respiratory fluctuation extraction unit 700 includes a frequency component suppression unit 701, a fourth spectrum storage unit 702, and an IFFT unit 703.

The frequency component suppression unit 701 reads out the first spectrum from the first spectrum storage unit 40, and reads out the respiratory cycle of the user from the respiratory cycle storage unit 50. The frequency component suppression unit 701 suppresses frequency components that do not correspond to the respiratory cycle of the user within the first spectrum (in other words, extracts frequency components that correspond to the respiratory cycle of the user within the first spectrum), and generates a fourth spectrum. The frequency component suppression unit 701 saves the fourth spectrum to the fourth spectrum storage unit 702.

Figure 22:
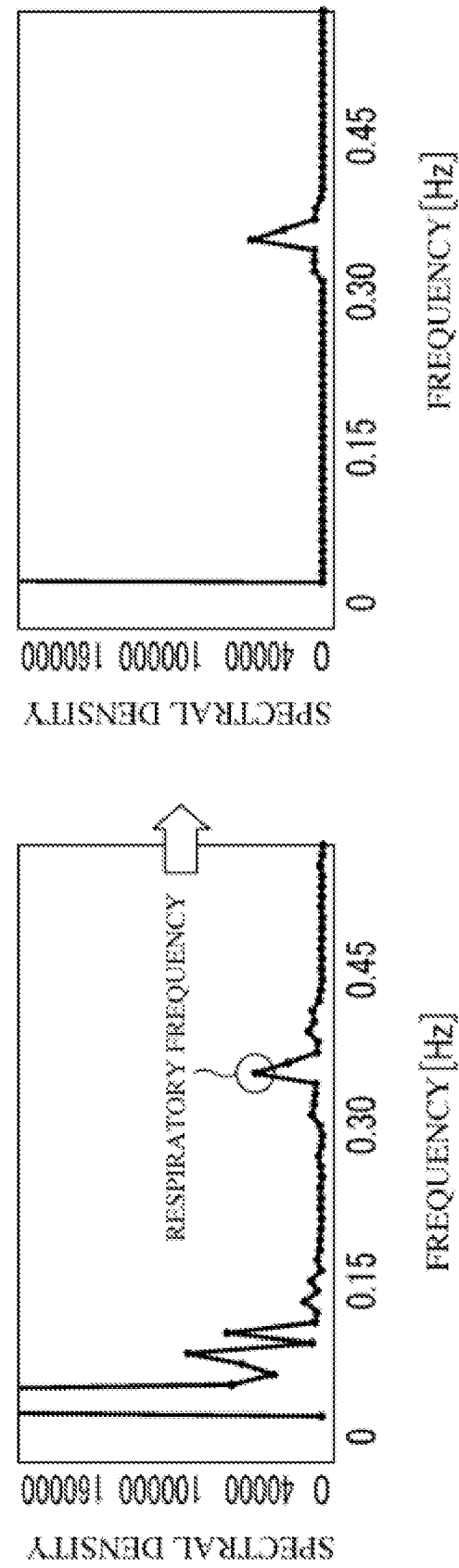
FIG. 22 is an illustrative diagram of operations of a frequency component suppression unit of FIG. 20.

The frequency component suppression unit 701 may, for example, perform band-pass filtering that includes the respiratory frequency corresponding to the respiratory cycle of the user in the passband or high pass filtering in which the cutoff frequency is set to lower than the respiratory frequency. The components of the respiratory frequency of the user will be thereby extracted, as illustrated in FIG. 22.

The fourth spectrum storage unit 702 stores the fourth spectrum generated by the frequency component suppression unit 701. The fourth spectrum stored in the fourth spectrum storage unit 702 is read out by the IFFT unit 703 as needed.

The IFFT unit 703 reads out the fourth spectrum from the fourth spectrum storage unit 702. The IFFT unit 703 performs IFFT on the fourth spectrum, and generates respiratory fluctuation data, which is a time domain representation of the fourth spectrum. The IFFT unit 703 saves the respiratory fluctuation data to the respiratory fluctuation data storage unit 70. The IFFT unit 703 may be replaced by another frequency-time transformation unit.

Figure 23:
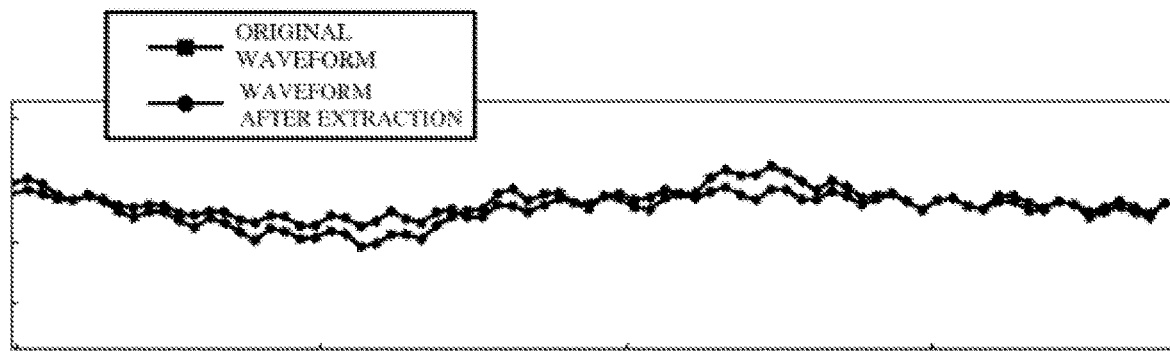
FIG. 23 is a graph illustrating the waveform (original waveform) of second blood pressure data and the waveform (waveform after respiratory fluctuation extraction) of respiratory fluctuation data.

FIG. 23 illustrates the waveform (original waveform) of the second blood pressure data and the waveform (waveform after respiratory fluctuation extraction) of the respiratory fluctuation data. Note that the second blood pressure data and respiratory fluctuation data in FIG. 23 correspond to the power spectra illustrated in FIG. 22. Because cyclic vibration due to respiratory fluctuation has been extracted from the respiratory fluctuation data, this data is suitable for analysis of respiratory fluctuation of the user such as pulsus *paradoxus*.

Figure 21:
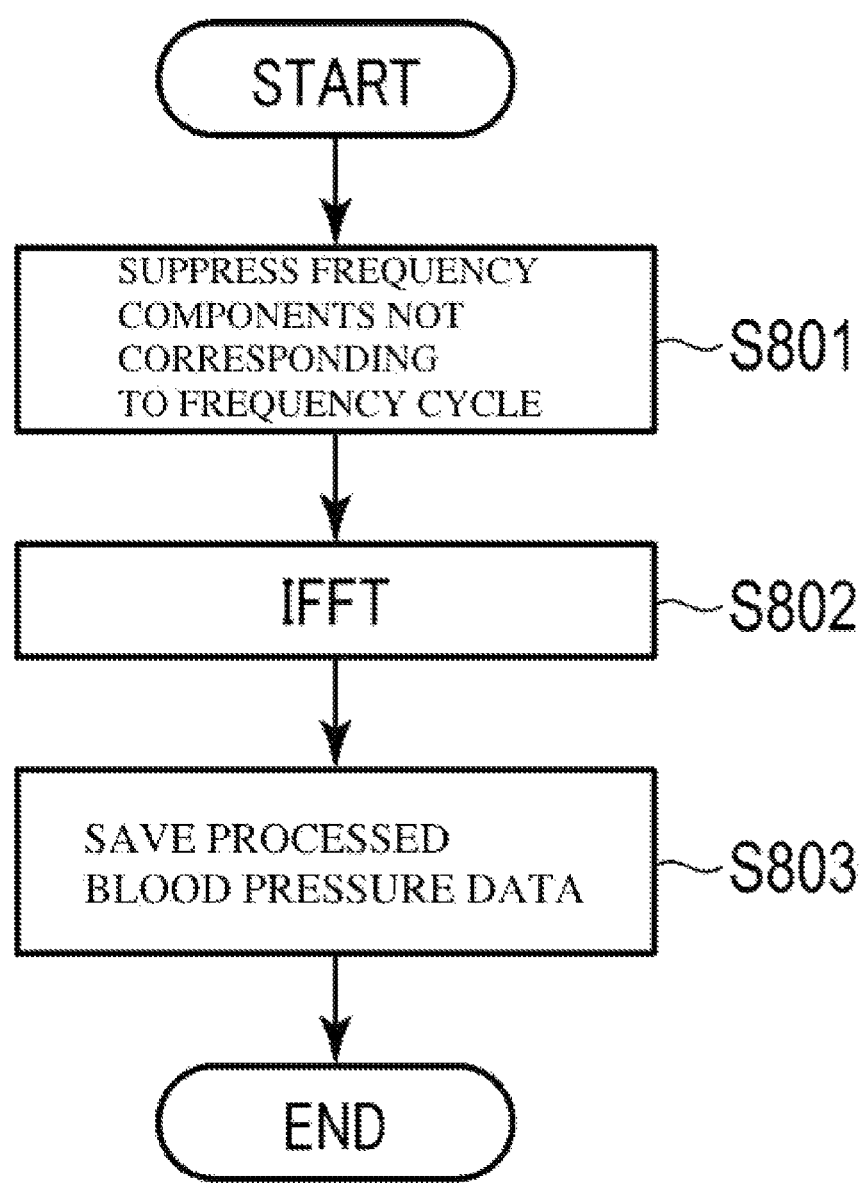
FIG. 21 is a flowchart illustrating step S800 of FIG. 19 in detail.

Step S800 of FIG. 19 is illustrated in detail in FIG. 21.

The frequency component suppression unit 701 suppresses frequency components that do not correspond to the respiratory cycle of the user inferred in step S500 of FIG. 19 within the first spectrum, and generates a fourth spectrum (step S801).

The IFFT unit 703 performs IFFT on the fourth spectrum generated in step S801, and generates respiratory fluctuation data, which is a time domain representation of the fourth spectrum (step S802). The IFFT unit 703 saves the respiratory fluctuation data generated in step S802 to the respiratory fluctuation data storage unit 70 (step S803).

As described above, the blood pressure data processing apparatus according to the second embodiment generates respiratory fluctuation data from which the respiratory fluctuation of the user has been extracted, using the inferred respiratory cycle. Therefore, according to this blood pressure data processing apparatus, respiratory fluctuation data suitable for analysis of respiratory fluctuation of the user (e.g., pulsus *paradoxus*) can be obtained.

Third Embodiment

Figure 24:
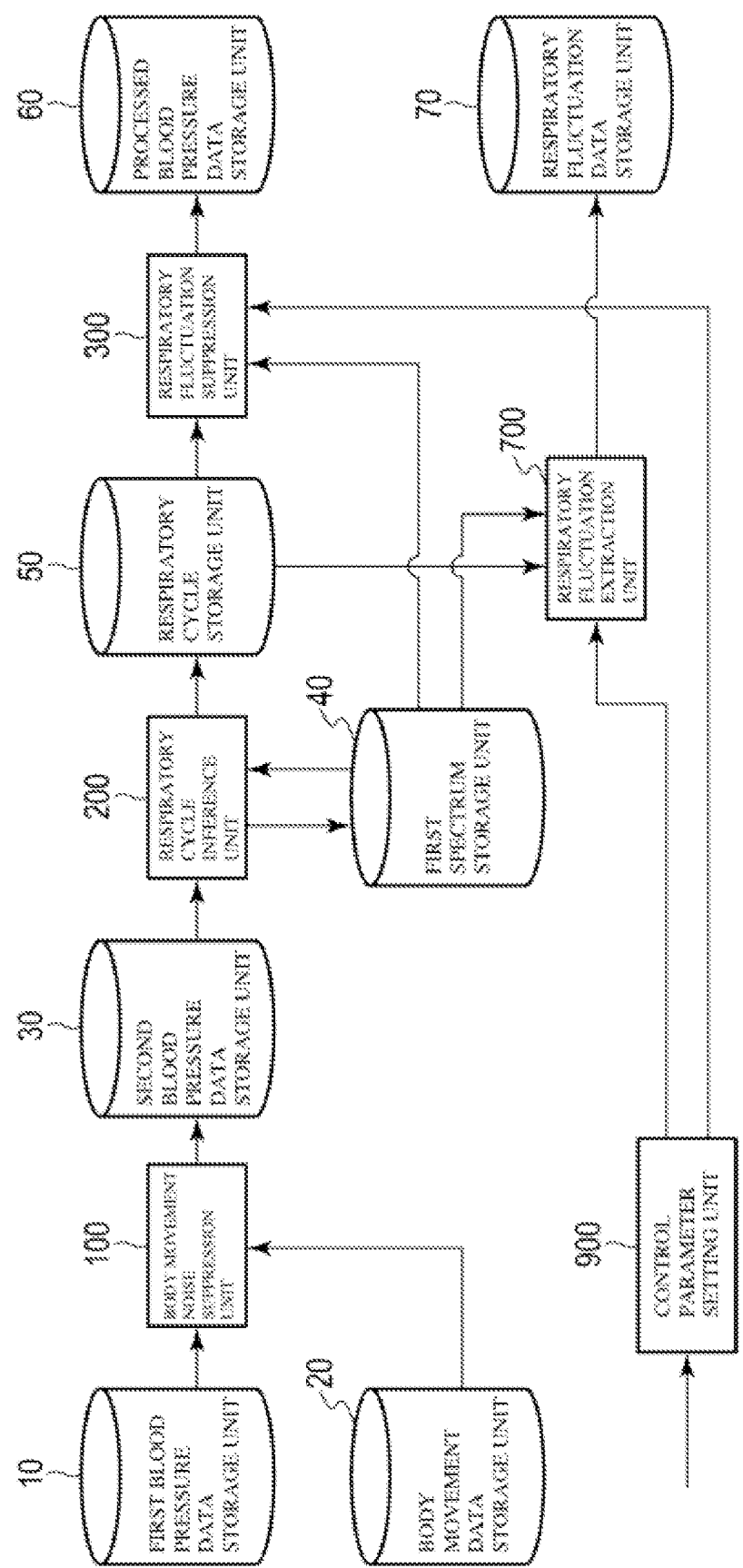
FIG. 24 is a block diagram illustrating a blood pressure data processing apparatus according to a third embodiment.

As illustrated in FIG. 24, the blood pressure data processing apparatus according to a third embodiment includes a first blood pressure data storage unit 10, a body movement data storage unit 20, a body movement noise suppression unit 100, a second blood pressure data storage unit 30, a respiratory cycle inference unit 200, a first spectrum storage unit 40, a respiratory cycle storage unit 50, a respiratory fluctuation suppression unit 300, a processed blood pressure data storage unit 60, a respiratory fluctuation extraction unit 700, a respiratory fluctuation data storage unit 70, and a control parameter setting unit 900.

The control parameter setting unit 900 sets a first control parameter indicating that processing for suppressing respiratory fluctuation is enabled/disabled, and sets a second control parameter indicating that processing for extracting respiratory fluctuation is enabled/disabled. The first control parameter and the second control parameter may be designated by the user, who is the person whose blood pressure is to be measured, or another person (e.g., doctor, health instructor or manufacturer, retailer or administrator of blood pressure data processing apparatus), or may be determined automatically. The control parameter setting unit 900 notifies the set first control parameter to the respiratory fluctuation suppression unit 300, and notifies the set second control parameter to the respiratory fluctuation extraction unit 700.

By making the first control parameter settable, it becomes possible to select whether to execute/omit processing for suppressing respiratory fluctuation. Similarly, by making the second control parameter settable, it becomes possible to select whether to execute/omit processing for extracting respiratory fluctuation.

The respiratory fluctuation suppression unit 300 of FIG. 24 differs from the respiratory fluctuation suppression unit 300 of FIG. 1 in terms of performing processing for suppressing respiratory fluctuation in the case where the first control parameter indicates enabled, and not performing processing for suppressing respiratory fluctuation in the case where the first control parameter indicates disabled.

The respiratory fluctuation extraction unit 700 of FIG. 24 differs from the respiratory fluctuation extraction unit 700 of FIG. 18 in terms of performing processing for extracting respiratory fluctuation in the case where the second control parameter indicates enabled, and not performing processing for extracting respiratory fluctuation in the case where the second control parameter indicates disabled.

Figure 25:
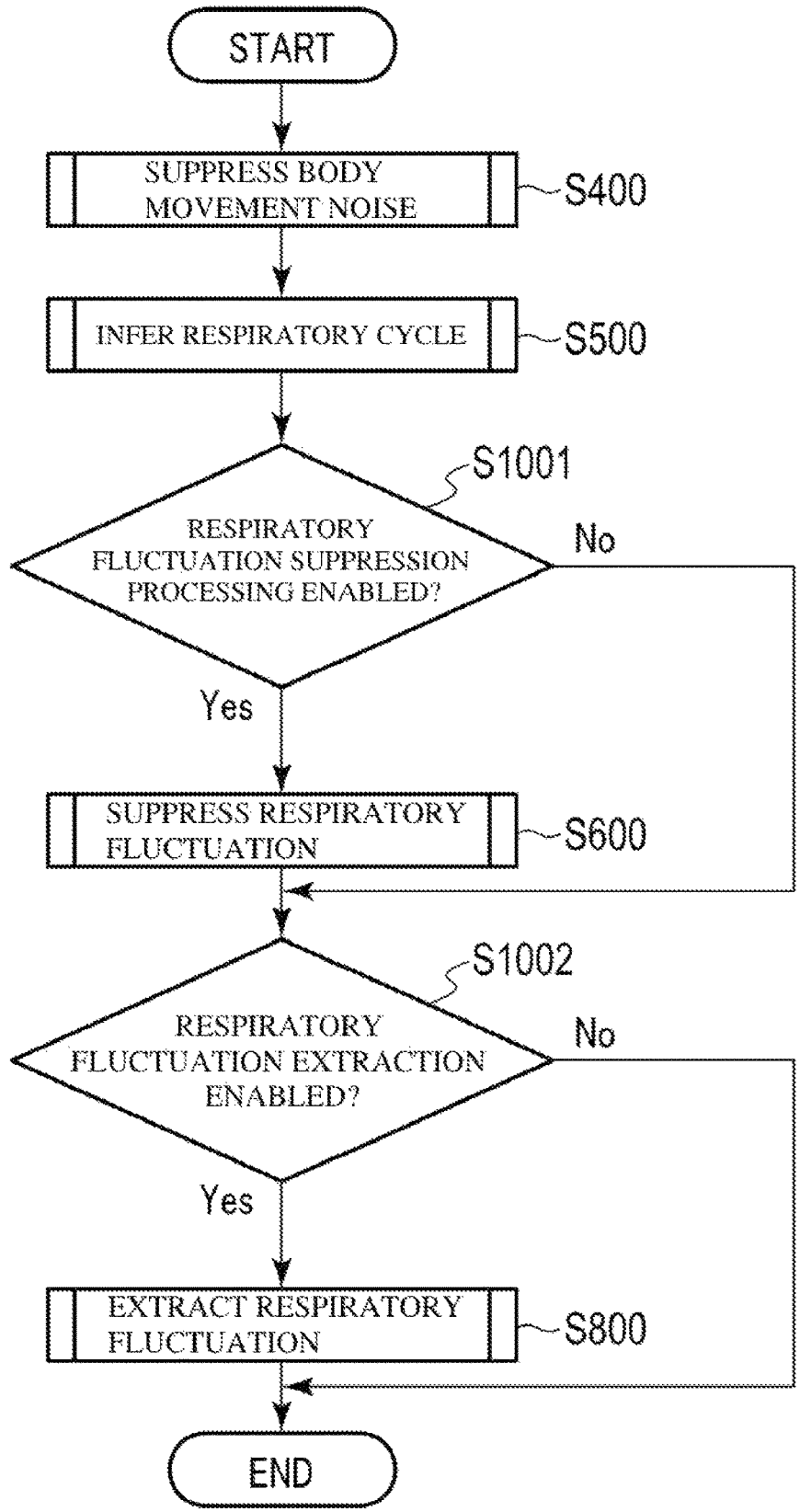
FIG. 25 is a flowchart illustrating operations of the blood pressure data processing apparatus of FIG. 24.

The blood pressure data processing apparatus of FIG. 24 operates as illustrated in FIG. 25. In FIG. 25, steps S400 and S500 can be similar to FIG. 2. Also, in FIG. 25, step S800 can be similar to FIG. 19.

Specifically, in FIG. 25, step S1001 for determining to execute/omit step S600 and S1002 for determining to execute/omit step S800 are provided after step S500. Note that steps S1001 and S1002 may be executed in a different order to FIG. 25, or may be executed as one step.

In step S1001, the respiratory fluctuation suppression unit 300 refers to the first control parameter set by the control parameter setting unit 900. In the case where the first control parameter indicates that processing for suppressing respiratory fluctuation is enabled, the processing advances to step S600, and if this is not the case, step S600 is omitted.

In step S1002, the respiratory fluctuation extraction unit 700 refers to the second control parameter set by the control parameter setting unit 900. In the case where the second control parameter indicates that processing for extracting respiratory fluctuation is enabled, the processing advances to step S800, and if this is not the case, step S800 is omitted.

As described above, the blood pressure data processing apparatus according to the third embodiment makes it possible to select whether to execute/omit processing for suppressing respiratory fluctuation described in the first embodiment and processing for extracting respiratory fluctuation described in the second embodiment. Therefore, according to this blood pressure data processing apparatus, processed blood pressure data suitable for analysis of blood pressure fluctuations (e.g., blood pressure surges) caused by factors other than the user's breathing and respiratory fluctuation data suitable for analysis of respiratory fluctuations (e.g., pulsus *paradoxus*) of the user can both be obtained as needed.

The above embodiments merely show examples for aiding understanding of the concepts of the present invention, and are not intended to limit the scope of the invention. In the embodiments, addition, deletion or substitution of various constituent elements can be carried out without departing from the spirit of the invention.

Various functional units described in the above embodiments may be realized by using a circuit. The circuit may be a dedicated communication circuit that realizes a specific function, or a may be a general-purpose circuit such as a processor.

The processing of the above embodiments can be at least partially realized by using a general-purpose computer as basic hardware. Programs that realize the above processing may be provided by being stored on a computer-readable recording medium. Programs are stored on the recording medium as installable files or executable files. Exemplary recording media include magnetic disk, optical disk (CD-ROM, CD-R, DVD, etc.), magneto-optical disk (MO, etc.), and semiconductor memory. Any recording medium that is able to store programs and is readable by computer may be applied. Also, programs that realize the above processing may be stored on a computer (server) connected to a network such as the Internet, and downloaded to a computer (client) via the network.

The above embodiments can be partially or wholly described as in the following supplementary note, apart from the claims, but are not restricted thereto.

Supplementary Note 1

A blood pressure data processing apparatus including:
a memory; and
a processor connected to the memory,
the processor being configured to:
(a) select one of peak frequencies indicating a peak in power spectra of a first spectrum, which is a frequency domain representation of second blood pressure data in which noise relating to body movement of the user included in first blood pressure data of the user is suppressed;
(b) suppress a component of the selected peak frequency within the first spectrum, and generate a second spectrum;
(c) calculate a first respiratory fluctuation in the second blood pressure data, and calculate a second respiratory fluctuation in third blood pressure data, which is a time domain representation of the second spectrum;
(d) calculate an attenuation amount of the second respiratory fluctuation relative to the first respiratory fluctuation; and
(e) determine a cycle corresponding to the selected peak frequency as the respiratory cycle of the user if the attenuation amount is greater than a first threshold.

The invention claimed is:
1. A blood pressure data processing apparatus comprising:
a respiratory cycle inference unit configured to infer a respiratory cycle of a user based on a first spectrum, which is a frequency domain representation of second blood pressure data in which noise relating to body movement of the user included in first blood pressure data of the user is suppressed,
wherein the respiratory cycle inference unit includes:
a peak selection unit configured to select one of peak frequencies indicating a peak in power spectra of the first spectrum;
a first frequency component suppression unit configured to suppress a component of the selected peak frequency within the first spectrum, and generate a second spectrum;
a respiratory fluctuation calculation unit configured to calculate a first respiratory fluctuation in the second blood pressure data, and calculate a second respiratory fluctuation in third blood pressure data, which is a time domain representation of the second spectrum;
an attenuation amount calculation unit configured to calculate an attenuation amount of the second respiratory fluctuation relative to the first respiratory fluctuation; and
a respiratory cycle determination unit configured to determine a cycle corresponding to the selected peak fre- quency as the respiratory cycle of the user if the attenuation amount is greater than a first threshold, wherein the respiratory cycle determination unit causes the peak selection unit to select one of unselected peak frequencies if the attenuation amount is less than or equal to the first threshold.

2. The blood pressure data processing apparatus according to claim 1,
wherein the peak selection unit selects peak frequencies in descending order of frequency.

3. The blood pressure data processing apparatus according to claim 2,
wherein the first frequency component suppression unit performs low pass filtering on the first spectrum to generate the second spectrum, and
a cutoff frequency of the low pass filtering is set to lower than the selected peak frequency.

4. The blood pressure data processing apparatus according to claim 1, further comprising:
a respiratory fluctuation suppression unit configured to generate processed blood pressure data in which respiratory fluctuation of the user included in the second blood pressure data is suppressed,
wherein the respiratory fluctuation suppression unit includes:
a second frequency component suppression unit configured to suppress frequency components that correspond to the respiratory cycle of the user within the first spectrum, and generate a third spectrum; and
a first transformation unit configured to transform the third spectrum into a time domain representation, and generate the processed blood pressure data.

5. The blood pressure data processing apparatus according to claim 1, further comprising:
a respiratory fluctuation extraction unit configured to extract respiratory fluctuation of the user included in the second blood pressure data, and generate respiratory fluctuation data,
wherein the respiratory fluctuation extraction unit includes:
a third frequency component suppression unit configured to suppress frequency components that do not correspond to the respiratory cycle of the user within the first spectrum, and generate a fourth spectrum; and
a second transformation unit configured to transform the fourth spectrum into a time domain representation, and generate the respiratory fluctuation data.

6. The blood pressure data processing apparatus according to claim 1, further comprising:
a setting unit configured to set a first control parameter indicating that processing for suppressing the respiratory fluctuation of the user included in the second blood pressure data is enabled/disabled, and a second control parameter indicating that processing for extracting the respiratory fluctuation is enabled/disabled;
a respiratory fluctuation suppression unit configured to, in a case where the first control parameter indicates enabled, generate processed blood pressure data in which the respiratory fluctuation of the user included in the second blood pressure data is suppressed; and
a respiratory fluctuation extraction unit configured to, in a case where the second control parameter indicates enabled, extract the respiratory fluctuation and generate respiratory fluctuation data,
wherein the respiratory fluctuation suppression unit includes:
a second frequency component suppression unit configured to suppress frequency components that correspond to the respiratory cycle of the user within the first spectrum, and generate a third spectrum; and
a first transformation unit configured to transform the third spectrum into a time domain representation, and generate the processed blood pressure data, and
the respiratory fluctuation extraction unit includes:
a third frequency component suppression unit configured to suppress frequency components that do not correspond to the respiratory cycle of the user within the first spectrum, and generate a fourth spectrum; and
a second transformation unit configured to transform the fourth spectrum into a time domain representation, and generate the respiratory fluctuation data.

7. The blood pressure data processing apparatus according to claim 1, further comprising:
a body movement noise suppression unit configured to suppress noise relating to body movement of the user included in the first blood pressure data, and generate the second blood pressure data,
wherein the body movement noise suppression unit includes:
a body movement determination unit configured to determine whether body movement of the user has occurred in a unit period, based on body movement data obtained from a motion sensor worn by the user; and
a blood pressure data interpolation unit configured to generate blood pressure data through interpolation for a unit period with respect to which it is determined that body movement of the user has occurred, and replace the first blood pressure data of the unit period with the blood pressure data generated through interpolation to generate the second blood pressure data.

8. A blood pressure data processing program for causing a computer to function as the blood pressure data processing apparatus according to claim 1.

9. A blood pressure data processing method comprising:
inferring a respiratory cycle of a user based on a first spectrum, which is a frequency domain representation of second blood pressure data in which noise relating to body movement of the user included in first blood pressure data of the user is suppressed;
wherein inferring the respiratory cycle of the user includes:
selecting one of peak frequencies indicating a peak in power spectra of the first spectrum;
suppressing a component of the selected peak frequency within the first spectrum, and generating a second spectrum;
calculating a first respiratory fluctuation in the second blood pressure data, and calculating a second respiratory fluctuation in third blood pressure data, which is a time domain representation of the second spectrum;
calculating an attenuation amount of the second respiratory fluctuation relative to the first respiratory fluctuation; and
determining a cycle corresponding to the selected peak frequency as the respiratory cycle of the user if the attenuation amount is greater than a first threshold,
wherein, in the determining of the cycle, if the attenuation amount is less than or equal to the first threshold, one of unselected peak frequencies is caused to be selected.

* * * * *